United States Patent [19]

Bloch

[11] Patent Number: 5,856,192
[45] Date of Patent: Jan. 5, 1999

[54] PRECISION AND ACCURACY OF ANION-EXCHANGE SEPARATION OF NUCLEIC ACIDS

[75] Inventor: Will Bloch, San Mateo, Calif.

[73] Assignee: The Perkin-Elmer Corporation, Foster City, Calif.

[21] Appl. No.: 589,904

[22] Filed: Jan. 23, 1996

Related U.S. Application Data

[63] Continuation of Ser. No. 238,392, May 5, 1994, abandoned, which is a continuation-in-part of Ser. No. 60,477, May 11, 1993, abandoned, which is a continuation of Ser. No. 679,736, Apr. 3, 1991, abandoned.

[51] Int. Cl.$^6$ ..................................................... G01N 30/02
[52] U.S. Cl. ................................ 436/18; 435/6; 436/161; 536/25.4; 536/26.43; 564/281; 935/19
[58] Field of Search ............................. 435/6; 536/26.42, 536/26.43, 25.4; 935/19, 20; 436/161, 18; 564/281, 291

[56] References Cited

U.S. PATENT DOCUMENTS

| | | | |
|---|---|---|---|
| 4,039,382 | 8/1977 | Thang et al. . | |
| 4,110,360 | 8/1978 | Sheldon et al. . | |
| 4,115,216 | 9/1978 | Skaletz . | |
| 4,136,175 | 1/1979 | Rideout et al. | 424/180 |
| 4,560,447 | 12/1985 | Shono . | |
| 4,711,955 | 12/1987 | Ward et al. | 536/29 |
| 4,917,781 | 4/1990 | Sharifian et al. . | |
| 4,935,342 | 6/1990 | Seligson et al. . | |
| 4,950,368 | 8/1990 | Weinberg et al. . | |
| 4,965,199 | 10/1990 | Capon et al. | 435/320 |
| 5,010,183 | 4/1991 | Macfarlane . | |
| 5,087,559 | 2/1992 | Smith et al. | 435/6 |
| 5,118,672 | 6/1992 | Schinazi et al. | 514/47 |
| 5,175,269 | 12/1992 | Stavrianopoulos | 536/27 |
| 5,702,896 | 12/1997 | Collins et al. . | |

FOREIGN PATENT DOCUMENTS

| | | |
|---|---|---|
| 0270017 | 11/1987 | European Pat. Off. . |
| 3910856 | 11/1989 | Germany . |
| 9100145 | 1/1991 | WIPO . |

OTHER PUBLICATIONS

Spittler et al., J. Chromatogr. vol. 317 pp. 527–531, 1984.
Robinson and Grant, 1966, J. Biol. Chem. 241:4030–4042.
Shapiro et al, 1969, Biochemistry 8:3219–3232.
Shapiro et al, 1969, Biochemistry 8:3233–3241.
Melchior and von Hippel, 1973, Proc. Natl. Acad. Sci. USA 70:298–302.
Orosz and Wetmur, 1977, Biopolymers 16:1183–1199.
Shore et al, 1981, Proc. Natl. Acad. Sci. USA 78:4833–4837.
Kato et al, 1983, J. Chromatography 265:342–346.
Hagerman, 1985, Biochemistry 24:7033–7037.
Hecker et al, 1985, J. Chromatography 326:251–261.
Eriksson et al, 1986, J. Chromatography 359:265–274.
Muller, 1986, European Journal of Biochemistry 155:203–212.
Thompson, 1986, BioChromatography 1(1):16–20.
Zon and Thompson, 1986, BioChromatography 1(1)22–32.
Thompson, 1986, BioChromatography 1(2):68–80.
Thompson, 1987, BioChromatography 2(1):4–18.
Westman et al, 1987, Anal. Biochem. 166:158–171.
Koo and Crothers, 1988, Proc. Natl. Acad. Sci. USA 85:1763–1767.
Merion et al, 1988, BioTechniques 6:246–251.
Kato et al, 1989, J. Chromatography 478:264–268.
Hagerman, 1990, Annual Reviews of Biochemistry 59:755–781.
Maa et al, 1990, J. Chromatography 508:61–73.
Journal of Chromatography, vol. 467(1990), No. 1, pp. 217–226, Ellegren et al, Size–Exclusion Chromatography of DNA Restriction Fragments — Fragment Length Determinations and a Comparison with the Behavior of Proteins Size–Exclusion Chromatography.
Chemical Reviews, vol. 89(1989), pp. 309–319, Larry McLaughlin, "Mixed–Mode Chromatography of Nucleic Acids".
Journal of Chromatography, vol. 533(1990), pp. 87–96, R.G. Brownlee et al, "Application of Capillary DNA Chromatography to Detect AIDS Virus (HIV–1) DNA in Blood".
Journal of Chromatography, vol. 359(1986), pp. 265–274, S. Eriksson et al, "Separation of DNA Restriction Fragments by Ion–Pair Chromatography".
Nucleic Acids Research, vol. 19(1991), pp. 4181–4188, F. Fach et al, "DNA Fragments Display Retarded Elution upon Anion–Exchange HPLC".

*Primary Examiner*—Jan Ludlow
*Attorney, Agent, or Firm*—Paul D. Grossman

[57] ABSTRACT

Solvents for salt-gradient anion-exchange separation of nucleic acids, especially double-stranded DNA and especially by liquid chromatography, are improved by replacing NaCl as the eluting salt with any of a wide range of alkyl ammonium salts and can be used to elute nucleic acids in strict order of increasing length, with reduced sensitivity to elution temperature and salt concentration. Anion-exchange chromatography with these solvents is well suited for identification of DNA fragments on the basis of size, with greater accuracy, precision, and resolvable size range than often is possible with gel electrophoresis.

10 Claims, 10 Drawing Sheets

PRECISION AND ACCURACY OF ANION-EXCHANGE SEPARATION OF NUCLEIC ACIDS

This application is a continuation of Ser. No. 08/238,392, filed May 5, 1994, now abandoned, which is a continuation-in-part of Ser. No. 08/060,477, filed May 11, 1993, now abandoned which is a continuation of Ser. No. 07/679,736, filed Apr. 3, 1991, now abandoned.

BACKGROUND OF THE INVENTION

1. Field of the Invention

This invention relates to novel solvents for the anion-exchange separation of nucleic acid fragments. These solvents result in the marked improvement of chromatographic methods for the analysis of nucleic acids in molecular biology, analytical biochemistry, clinical chemistry, industrial and environmental microbiology, and molecular genetics.

2. Description of Related Art

A single strand of DNA consists of a chain of deoxyribose-phosphate monomers covalently linked via phosphodiester bonds and also contains a single aromatic heterocyclic "base" covalently attached to each deoxyribose ring. In aqueous solvents of pH greater than about 2, the very hydrophilic sugar-phosphate polymer backbone contributes one negative charge for each phosphodiester plus one or two negative charges for every terminal phosphomonoester. Therefore, DNA is a polyanion; the net negative charge is almost perfectly proportional to chain length. However, the bases are very hydrophobic, so that a single strand has mixed hydrophilic-hydrophobic character. Single-stranded DNA adopts a random-coil conformation which fluctuates constantly and rapidly and has a time-averaged spherical shape. Within the sphere, random hydrophobic aromatic stacking interactions and base pairing hydrogen bonds tend to draw together different parts of the chain, and electrostatic repulsion of the phosphate groups tends to drive apart different parts of the structure. The balance between these opposing tendencies and therefore the average spherical diameter depend on temperature and solvent composition, especially ionic strength.

Most naturally occurring DNA is double-stranded, consisting of two single strands of similar or identical length which interact noncovalently to form a double helix in which the four commonly occurring bases, adenine (A), thymine (T), guanine (G), and cytosine (C), exist in complementary sequences on the two interacting strands, such that each A on one strand is hydrogen-bonded to T on the other strand (and vice versa) and each G on one strand is hydrogen-bonded to a C on the other strand (and vice versa). This base-paired structure sequesters the hydrophobic groups inside the double helix along its axis and away from the solvent; the two helical sugar-phosphate chains spiral down the outside of the double-stranded structure, presenting a hydrophilic, poly-anionic face to the solvent. Two helical groves of different width, "major" and "minor," separate the two sugar-phosphate chains. The grooves are large enough to bind water molecules and solvent cations. The double-helical structure also stiffens double-stranded DNA so that segments less than several hundred base pairs are effectively rigid and linear rather than flexibly coiled into a sphere. On the length scale of many hundreds to thousands of base pairs, double-stranded DNA also is coiled but much more loosely than single-stranded DNA. Recently it has become clear that certain sequences in double-stranded DNA induce curvature in the double helix so that it no longer is linear on the length scale of tens to hundreds of base pairs (reviewed by Hagerman, 1990, Annual Reviews of Biochemistry 59:755–781).

Double-stranded DNA can be reversibly "melted" to yield two chains of single stranded DNA by heating to temperatures in the approximate range of 50°–100° C. G-C base pairs tend to melt at higher temperatures than A-T base pairs because their base pairing interactions are stronger. Solvent composition also affects double-helix stability; adding an organic cosolvent or lowering the salt concentration in an aqueous solvent lowers the $T_m$ (the temperature where half of the DNA has dissociated into single strands) of any DNA, regardless of base composition.

RNA structure resembles but is more complex than DNA structure. The single strand is almost identical to the DNA single strand, differing only in the replacement of deoxyribose by ribose and of thymine by uracil (which still can base pair to adenine). However, double-stranded RNA is rare, although single strands often contain relatively short self-paired double-stranded regions because adjoining base sequences are complementary. RNA has the same polyanionic properties as DNA, but the abundance of single-stranded regions renders it more hydrophobic, and the mixture of single-stranded and double-stranded regions destroys the shape regularity (spherical or linear) seen in single- stranded and double-stranded DNA.

The most common methods for separating different DNA molecules, whether for preparative or for analytical purposes, exploit the strictly length-dependent polyanionic properties and the considerable shape regularity and flexibility of both single-stranded and double-stranded structures. Although most electrophoretic and chromatographic DNA separations depend directly or indirectly on polymer net charge, the near proportionality between charge and polymer length results in size-dependent differences in displacement of different DNA species along the separation axis (commonly expressed as distance in gel electrophoresis, time in capillary electrophoresis, and time or volume in chromatography). Larger molecules migrate more slowly and therefore travel less distance in any given electrophoretic separation, because the gel acts as a sieve to exert viscous drag on charged solute molecules; this drag varies directly with solute size. Most chromatographic separations of DNA entail gradient elution, wherein an eluting solute in the solvent is systematically and usually continuously increased with time of elution and volume of continuously flowing solvent; larger molecules are bound more tightly to the chromatographic resin than smaller molecules are, and therefore require higher concentrations of the chromatographic eluting solute to be displaced from the resin. Under ideal separation conditions electrophoretic migration rate and distance or chromatographic elution time and volume depend monotonically on DNA molecular size and can be used to identify specific DNA fragments according to size. In fully optimized separations, electrophoretic displacement or chromatographic elution time is a linear function of the logarithm of molecular size.

The identification value of a size-dependent nucleic acid separation depends on four performance characteristics: size range, size resolution, precision of movement, and size accuracy. Few separations give linear log size calibration curves over a range of more than one order of magnitude of molecular size. As many analyte systems include DNA species ranging over several orders of size magnitude, several different electrophoretic gels (e.g., employing different gel densities) or chromatographic elutions must be run to characterize the system fully. Size resolution concerns how small a difference in DNA length results in distinguishable electrophoretic bands or chromatographic peaks; high-resolution systems usually access the narrowest size ranges. Faster separations usually sacrifice size resolution. Precision of movement is the most important performance criterion for DNA identification. How reproducibly a particular fragment migrates a given distance or elutes at a given time absolutely determines confidence that a fragment has a particular size and is not a completely different species. Precision limitations of both electrophoretic and chromatographic separations are reduced by frequent running of external molecular size standards in adjacent gel lanes or in a consecutive chromatographic separation and optimally by running internal molecular size standards together with the test sample, taking care that the standards do not interfere with the analyte bands or peaks. Molecular size accuracy refers to how exactly analyte species fall on a smooth calibration curve of migration distance or elution time versus molecular size (or its logarithm). Species which fall off the consensus calibration curve for the majority of size standards or analyte molecules may be assigned incorrect molecular size values, although they still can be correctly and precisely identified in test samples as long as the separation anomaly has been characterized previously with known samples. The major risk of size inaccuracy is mischaracterization of new analytes during research and discovery activities.

The total value of a separation method depends on performance in other ways besides the quality of the size information. Other important analytical properties include analyte quantitation (precision, accuracy, dynamic range, and detection limit), ease of recovery of separated species (for post-separation study such as DNA sequencing), reliability (freedom from interferences, equipment or reagent malfunction, and operator error), speed (time per sample), throughput (samples per hour, day or work week), and cost (in equipment, reagents, and labor, including labor quantity and quality).

In recent years, gel electrophoresis has become the standard method for size dependent nucleic acid separations. Two gel matrices are commonly used: agarose, which is easier to use but which gives lower size resolution, and polyacrylamide, which is harder and more hazardous to use and which gives the best size resolution, up to the maximum possible performance (in sufficiently long gels) of resolving single nucleotide differences, especially for single-stranded DNA. Any given gel density provides no more than about one order of magnitude of practical DNA size range. Size precision is rarely measured or expected; gel or electric field inhomogeneity often results in inconsistent migration among lanes or within a single lane in a slab gel. Species generally are identified by approximate movement relative to other species; and absolute analyte identification is based on nucleic acid probing, most commonly by dot blotting or Southern analysis, which gives a positive signal only if the separated species contains base sequence complementary to a polynucleotide or oligonucleotide of known sequence. Identification by blotting generally is slow, labor-intensive, and relatively unreliable, and often is hazardous because the analytical signal commonly is created by radioactive tags on probes.

Gel electrophoresis is unreliable with respect to double-stranded DNA size accuracy, because the molecular curvature described above can retard electrophoretic migration sufficiently to imply that a molecule is twice as long as it really is (Koo and Crothers, 1988, *Proc. Natl Acad. Sci. USA* 85:1763–1767; Hagerman, 1985, *Biochemistry* 24:7033–7037; and Shore et al, 1981, *Proc. Natl. Acad. Sci. USA* 78:4833–4837). Gel electrophoresis has other performance limitations. Bands are most commonly visualized by staining with ethidium, which shows strong fluorescence enhancement when it binds to double-stranded (but not single-stranded) DNA. Such staining is hazardous because ethidium is a cancer-suspect agent; it is very insensitive to single-stranded DNA; it is unreliable for quantitating electrophoretically separated species, because the reversible dye binding reaction is very sensitive to experimental conditions, and fluorescence requires careful calibration. Gel electrophoresis is labor-intensive and vulnerable to operator variability or error. It is relatively slow (at least several hours per run, including staining or other post-electrophoretic detection) but has acceptable throughput because several tens of samples can be run simultaneously. Recovery of separated species from the gel is slow and labor intensive.

Capillary electrophoresis has recently evolved to provide fast, high-resolution, size-dependent DNA separations which are very sensitive to low amounts (in mass units) of DNA. However, size precision is poor; quantitation of individual species is difficult and insensitive (with respect to DNA concentration, which is more important to molecular biologists and clinical chemists than DNA mass; DNA usually is abundantly obtainable, but often at relatively low concentrations); recovery of separated species in useful quantities is difficult because the mass of DNA processed in each separation is very small.

Liquid chromatography, and high-pressure liquid chromatography (HPLC) in particular, is still maturing as a DNA separation method (reviewed by Thompson, 1986, *BioChromatography* 1:16–20, 22–32, and 68–80; 1987, *BioChromatography* 2:4–18). The separation chemistry is independent of separation pressure; the latter variable varies inversely with the particle size of the chromatographic matrix and the time required for a separation. Separations that take many hours and hundreds of ml of solvent when run at atmospheric pressure on large- particle adsorbents can be completed in 3–30 minutes consuming 3–30 ml of solvent, at pressures of 5–10 atmospheres on 2–10 $\mu$m—diameter particles. Quantitative sensitivity is inversely proportional to separation volume, and HPLC is a highly automated procedure which makes little demands on labor quality or quantity. Liquid chromatography normally detects DNA via its high ultraviolet (UV) absorbance at a wavelength of maximum absorbance ($\lambda_{max}$) near 260 nm. HPLC is so automated that a single computer-controlled instrument can run the separation, measure eluted absorbance as a function of elution time, analyze the resulting elution profile to quantitate the absorbance in each peak (corresponding to a different DNA species), identify each peak in terms of elution time and even (by comparison to a calibration curve stored in the computer) molecular size, and collect each peak in a separate container for further analysis. The extreme sensitivity of HPLC UV absorbance detectors gives confident quantitation of peaks no higher than $10^{-4}$ absorbance units, containing approximately $10^{-10}$ g of nucleic acid in less than 0.1 ml of chromatographic solvent. Spectrophotometrically monitored HPLC has a lower DNA detection limit for double-stranded DNA than ethidium-stained gel electrophoresis. The broad dynamic range of HPLC UV absorbance detectors, measuring absorbances up to about 1 absorbance unit, allows HPLC to quantitate DNA ranging over 4 orders of magnitude in concentration, with none of the calibration difficulty of fluorescence measurements.

Two major liquid chromatographic separation chemistries are used for DNA: anion exchange and ion-paired reverse-phase. In anion exchange, the solid chromatographic matrix contains on its surface abundant fixed positive charges which bind the DNA polyanion with a strength related directly to DNA length. As the concentration of an eluting salt is increased, usually continuously with elution time and the volume of solvent passed through a cylindrical column of the densely packed matrix, DNA fragments are eluted in approximate order of increasing size, because dissolved salt weakens the binding of polyanion to matrix. In ion-paired reverse-phase separations, the solid chromatographic matrix contains on its surface abundant fixed hydrophobic groups, and the solvent contains a hydrophobic tetraalkylammonium or trialkylammonium chloride, bromide, or acetate salt. The alkylammonium cations bind weakly to the DNA polyanion to render it approximately electrically neutral and hydrophobic, and the hydrophobic DNA-alkylammonium complex binds to the hydrophobic matrix. As the concentration of a low-polarity organic cosolvent in the aqueous solvent is increased, usually continuously, over elution time, the hydrophobic interactions between DNA and matrix is weakened. Longer DNA molecules bind more tightly to the matrix than small ones, so that elution order again approximately parallels molecular size; larger DNA molecules require higher organic cosolvent concentrations to be eluted.

Despite the previously described advantages of HPLC as a reliable, economical, sensitive, quantitative method of analyzing DNA, neither separation chemistry is optimal with respect to size resolution, range, precision, or accuracy. Ion-paired reverse-phase separations tend to be slow (requiring several hours), often result in relatively low recoveries of eluted fragments, and give occasional inversions in retention time as a function of molecular size, jeopardizing their value for size-accurate identification (Erikson et al, 1986, *J. Chromatography* 359:265–274). The aqueous solvents used for these separations contain relatively low ($10^{-3}$–$10^{-1}$M) concentrations of trialkylammonium (e.g., triethylammonium) or tetraalkylammonium (e.g., tetrabutylammonium) salts and vary the concentration of an eluting organic cosolvent such as acetonitrile over the range of 5–50%.

Prior to the present invention, anion-exchange HPLC separation of double-stranded DNA on a variety of different ion-exchange solids has suffered from occasional to frequent inversions in retention time as a function of molecular size, preventing its use for size-accurate fragment identification (Kato et al, 1983, *J. Chromatog.* 265:342–346; Merion et al., 1988, *BioTechniques* 6:246–251; Kato et al., 1989, *J. Chromatog.* 478:264–268; Maa et al, 1990, *J. Chromatog.* 508:61–73; Muller, 1986, *Eur. J. Biochem.* 155:203–212; Hecker et al. 1985, *J. Chromatog.* 326:251–261; and Westman et al., 1987, *Anal. Biochem.* 166: 158–171). In almost every case, it has been remarked that the DNA fragments most likely to have retention times longer than predicted on the basis of molecular size also have abnormally high AT content. However, no remedy was proposed or demonstrated for this effect and only one theory, curvature of A-T rich DNA, has been suggested to explain it (Hecker et al, supra). In almost every case, the eluting salt was NaCl, generally varied in the concentration range of 0.3–1.2M. The other alkali metal chloride salts have been tried without evidence of improved performance over NaCl, and some eluting salt anions such as acetate, trichloroacetate, chlorate, and sulfate, gave greatly reduced fragment resolution or no separation at all (Westman et al. and Hecker et al., supra).

It generally has been observed that the salt gradient must be rendered increasingly shallow to resolve fragments of increasing size, up to the point that for one anion- exchange solid, very little size resolution occurred above 500 base pairs (Westman et al., supra). It has been suggested that this phenomenon occurs because DNA elution is controlled by salt activity rather than concentration (Muller, supra). Salts, including NaCl, show a drop in activity coefficient as salt concentration is increased in the 0.1M range. This drop renders salt activity less than proportional to salt concentration, increasing the salt concentration rise needed to obtain a given activity rise and therefore reducing the salt concentration sensitivity of retention time. However, in the 0.5–1.0M salt concentration range, activity coefficient becomes increasingly salt concentration-independent, rendering the salt activity more strongly salt concentration-dependent and therefore increasing the salt concentration-sensitivity of retention time.

In only one case (Muller, supra). has the effect of temperature on anion-exchange HPLC retention time been observed. Increasing temperature increased the strength of DNA binding to the anion-exchange solid, but no effort was made to quantitate the phenomenon or relate it to technical requirements for retention-time precision. Retention-time precision has not been a concern in the prior art.

The preceding review has focused on the HPLC of double-stranded DNA, expected to be simpler than that of single-stranded DNA and RNA, because partly- or completely single-stranded nucleic acid exposes bases to the solvent and the chromatographic matrix and therefore should show strongly sequence- and composition-dependent retention times. However, these complicating interactions can be reduced by including organic cosolvents in the eluting solvent, by choosing a chromatographic matrix which interacts minimally with the bases, or by operating at such a high pH, generally above 10, that some of the bases become anionic. When the bases bear negative charges, base-stacking and hydrogen bonding interactions among them are weakened, and the nucleic acid resembles a purely random coil, the radius and net charge of which are directly related to polymer length. Organic cosolvents promote this behavioral simplification in two ways, by weakening base-stacking and hydrogen bonding and by weakening base-matrix interactions.

Given the observation that high A-T content tends to cause double-stranded DNA to bind to anion-exchange solids more tightly than expected simply on the basis of molecular size, the following question arises: could some simple change in eluting conditions, such as temperature or solvent composition, ablate whatever structural difference between A-T-rich and G-C-rich DNA is responsible for the phenomenon?

Melchior and von Hippel, 1973, *Proc. Natl. Acad. Sci. USA* 70 :292–302, showed that tetraalkylammonium halide salts (especially tetramethylammonium chloride and tetraethyl-ammonium chloride) and at least one trialkylammonium salt (triethylammonium chloride) greatly reduced and could even eliminate the differences in melting behavior between G-C-rich and A-T-rich DNA. However, tetramethylammonium ion and tetraethylammonium ion had dramatically opposite effects on double-stranded DNA stability; the former increased $T_m$ whereas the latter decreased $T_m$. These effects were most evident at very high (greater than 2M) salt concentrations, one to two orders of magnitude higher than the concentration ranges in which these salts are used in ion-paired reverse-phase HPLC of nucleic acids. Shapiro et al., 1969, *Biochemistry* 9:3219–3232, showed that polylysine preferentially binds to and precipitates A-T-rich DNA and that adding tetraalkylammonium salts at very high concentration destroys and even reverses this preference.

The second phenomenon implies that the tetraalkylammonium ions also bind preferentially to A-T-rich DNA; this inference explains the results of Melchior and von Hippel as well. Shapiro et al., 1969, *Biochemistry* 9:3233–3241, showed directly that several tetraalkylammonium ions bind more tightly to A-T-rich than to G-C-rich DNA and suggested that this phenomenon, not seen for the alkali metal cations, arose from the tightness of steric fit of the tetraalkylammonium ions in the double helix major groove. Orosz and Wetmur, 1977, *Biopolymers* 16: 1183–1199, explored the steric interpretation by probing the effects on double-stranded DNA stability of a variety of tetraalkylammonium ions containing different combinations of methyl, ethyl, propyl, butyl, pentyl, and hexyl groups. Increasing alkyl group size tended to render the cation more helix-destabilizing and, for alkyl groups larger than ethyl, tended to reduce the ability to stabilize A-T-rich regions preferentially.

The question raised by these indications of preferential binding of tetraalkylammonium and trialkylammonium salts to A-T-rich regions of double-stranded DNA is whether such a preference could reduce the tendency of A-T-rich double-stranded DNA to bind especially tightly to anion-exchange solids. If alkylammonium cations could operate in this fashion in concentration range, presumably near 1M where they might elute DNA from anion-exchange matrices, then they might render anion-exchange HPLC an accurate method of estimating DNA fragment size from chromatographic retention time. Furthermore, the observation that double-stranded DNA affinity for at least one anion-exchange solid increases with increasing temperatures (Muller, supra) suggests that interactions of the eluting cation with DNA and of the eluting anion with anion-exchange solid may control the temperature dependence. If the DNA-anion-exchange-solid interaction alone controlled the temperature dependence, affinity would fall as the temperature is increased. Therefore, alkylammonium eluting salts might change the temperature sensitivity of chromatographic retention time. The lower this temperature sensitivity, the easier it would be to attain high retention-time precision, improving the ability of HPLC to identify DNA fragments solely on the basis of retention time.

Although the choice of eluting salt cation has the best chance of influencing the size accuracy of anion-exchange HPLC of double-stranded DNA, the choice of salt anion has strong effects, positive or negative, on the quality of the separation. As noted above, some anions reduce peak resolution on at least some anion-exchange solids. Anions have profound effects on double-stranded DNA stability (Robinson and Grant, 1966, *J. Biol. Chem.* 241:4030–4042); salt anions which tend to melt DNA might increase retention-time sensitivity to DNA A-T content or sequence. Salt anion interaction with the anion-exchange solid will affect retention-time temperature dependence, because it contributes to the total enthalpy change of the anion-exchange process. In this regard, anions which bind weakly to the anion- exchange solid are preferred because they are likely to contribute the smallest enthalpy changes. Finally, the chloride anion, almost universally used in the eluting buffers for DNA anion-exchange chromatography, is well known to promote the corrosion of stainless steel, commonly used in HPLC pumps, fittings, columns, and tubing. Almost any other buffer anion would be preferred in the interest of improving HPLC hardware durability and minimizing contamination of columns and analytes with Fe(III).

The combination of cation and anion in the eluting salt can affect HPLC pump durability and maintenance in still another way. Small solvent leaks deposit elution solvent on moving parts. After the water evaporates, the buffer salts crystallize to form abrasive solids which scratch the pistons and seals. The especially high eluting salt concentrations of anion-exchange chromatography of DNA are particularly damaging to HPLC pumps and valves. However, eluting salts differ in crystalline hardness and shape and therefore in abrasive potential; NaCl is particularly abrasive whereas salts of alkylammonium cations and of carboxylate anions should form softer crystals. Some salts, like those between dialkylamines or trialkylamines and short-chain aliphatic carboxylic acids (for example, formic and acetic acids) have the additional advantage of being volatile, because the component acids and bases are volatile (tetraalkylammonium salts do not share this property). Volatile salts are less likely to abrade moving parts and also are easier to remove from recovered samples of chromatographed DNA if they interfere with post-HPLC processing.

Clearly, optimizing solvent composition for the anion-exchange HPLC of DNA involves multiple criteria, some of which may be mutually incompatible. It is equally clear that the conventional eluting salt, NaCl, is suboptimal for multiple reasons: (1) retention-time sensitivity to DNA A-T content, which reduces size accuracy, (2) a very high retention-time temperature sensitivity which reduces size precision, (3) an escalating retention-time sensitivity to salt concentration as DNA fragment size increases, resulting in a reduced practical size range, and (4) a propensity to damage HPLC hardware chemically and physically. The present invention provides improved HPLC solvents which address all of these concerns.

SUMMARY OF THE INVENTION

In a first aspect, the invention comprises a solvent optimized for the salt gradient elution of nucleic acids, especially double-stranded DNA, from anion-exchange solids, especially particulate chromatographic matrices. The essential components of this solvent are (a) an eluting salt in the 0.5–1.5M concentration range, comprising a di-, tri-, or tetra-alkylammonium cation and any of a variety of mono-anions including formate, acetate, perchlorate, nitrate, chloride, bromide, methane sulfonate, and ethane sulfonate, and (b) a buffer acid of pKa ranging from about 3.5 to 9.5, present at no greater concentration than about 0.05M and regulating the solvent pH between about 4 and about 9. Preferably the buffer acid is cationic, so that its conjugate base does not bind to the anion-exchange solid. One embodiment of this aspect of the invention also comprises nucleic acid. Another embodiment comprises a concentrated form of the anion-exchange solvent, convenient for manufacturing, storage, and shipping.

In a second aspect, the invention comprises the combination of the anion-exchange solvent, with or without nucleic acid, with an anion-exchange solid, particularly solids that have a synthetic organic polymeric backbone.

In a third aspect, the invention comprises a salt- gradient elution process for the anion-exchange separation of nucleic acids differing in molecular size, wherein the nucleic acids are bound to an anion-exchange solid, which then is washed with a series of the solvents of the first aspect of the invention in such a way that the eluting salt concentration is increased over time. After elution, the solvents are analyzed for nucleic acid by UV absorbance.

In a fourth aspect, the invention comprises an affinity separation process for resolving double-stranded DNA, single-stranded DNA, RNA, and/or mononucleotides or nucleosides, which depends on the greater affinity of aralkylamine ligands for single-stranded DNA, RNA, mononucleotides, and nucleosides than for double-stranded DNA under certain solvent conditions.

DESCRIPTION OF THE PREFERRED EMBODIMENTS

Advantages of the Invention

Figure 1:
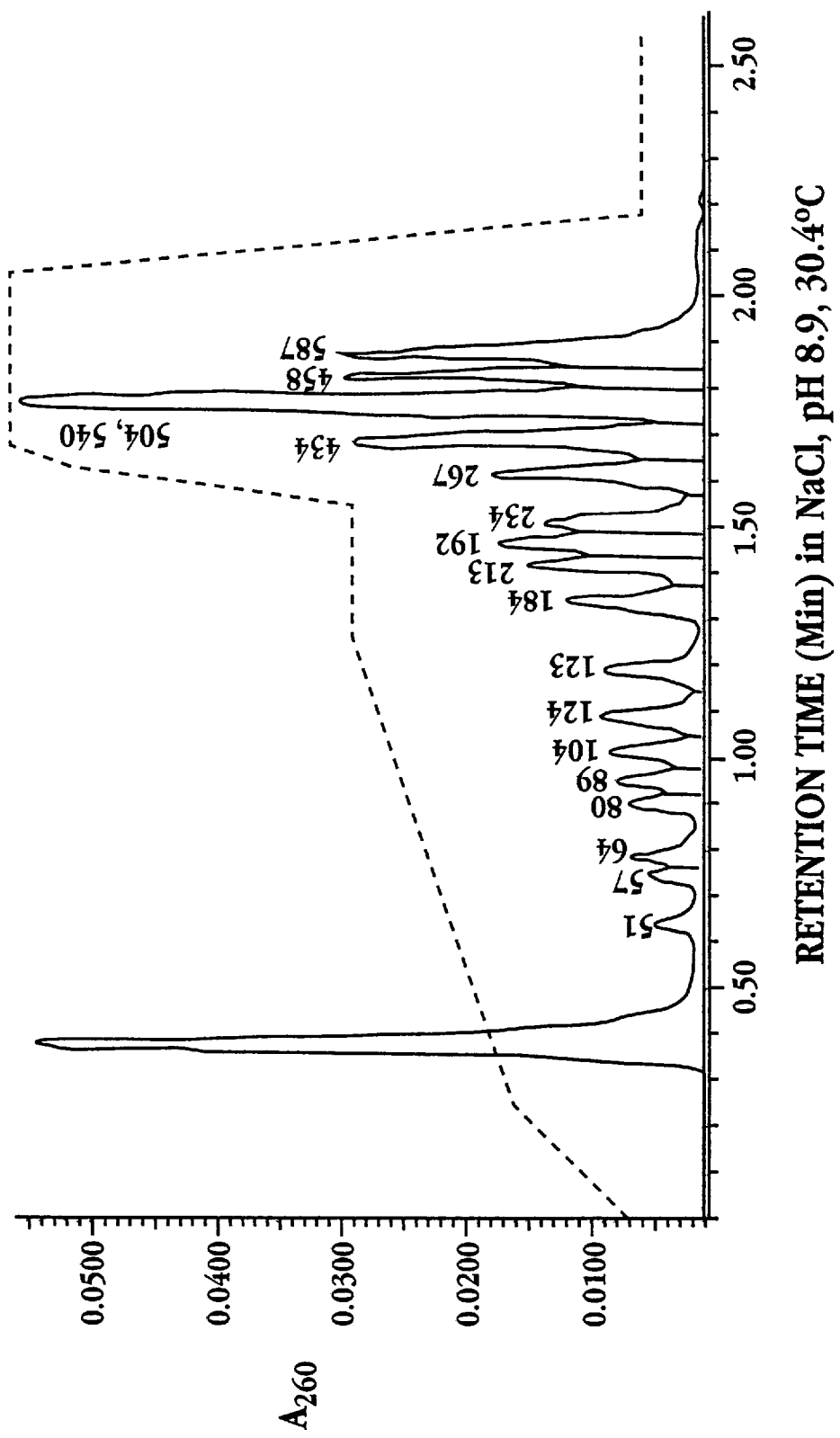
FIG. 1 shows an anion-exchange HPLC elution profile for the separation of the double-stranded DNA fragments created by digestion of plasmid pBR322 with restriction endonuclease HaeIII, wherein NaCl is used as the eluting salt.

This invention provides at least four improvements over the prior art for anion-exchange separation and analysis of nucleic acids, especially double-stranded DNA.

(1) It commonly is observed that nucleic acids, especially double-stranded DNA, are eluted from the anion-exchange solid in an order which depends on the base composition or base sequence of the nucleic acid as well as its length. Often separation strictly on the basis of length is most desirable, particularly as a way of identifying particular nucleic acid fragments. The anion-exchange solvents of the present invention are the first which consistently give length-dependent separation, permitting confident identification. They allow fast, automated, quantitatively accurate, anion-exchange processes such as HPLC to replace gel electrophoresis as the optimal mode of size dependent DNA identification. Gel electrophoresis is much slower, more labor intensive, less quantitative, and generally less reliable than HPLC.

(2) Confident DNA fragment identification on the basis of position in a chromatographic elution profile depends on the precision with which that position can be reproduced when different samples are chromatographed. Anion-exchange separations of double-stranded DNA, especially on synthetic organic polymeric anion-exchange solids, are extraordinarily temperature-sensitive when the conventional eluting salt, NaCl, is used. It is difficult to thermostat chromatographic separations closely enough to obtain the needed elution precision. The solvents of the present invention greatly reduce the temperature sensitivity of elution, providing greater precision in nucleic acid molecular size assignment without increasing the expense of the chromatographic equipment by requiring very precise thermostatting.

(3) Salt-gradient anion-exchange separation of double-stranded DNA requires an increasingly shallow gradient to resolve DNA fragments of increasing size. With conventional solvents using NaCl as the eluting salt, elution of fragments above about $10^3$ base pairs in length has poor size resolution because the salt gradient is too shallow to be controlled precisely by conventional chromatographic equipment. The anion-exchange solvents of the present invention reduce the degree to which the elution salt concentration sensitivity increases with nucleic acid molecular size, extending the practical size range over which anion-exchange chromatography has acceptable resolution.

(4) Conventional NaCl gradient elution of double-stranded nucleic acid from anion-exchange solids shows identical temperature sensitivity for fragments of different size. This phenomenon implies that resolution of fragments of different size cannot be improved by changing the elution temperature. The solvents of the present invention impart greater elution temperature sensitivity to larger fragments, permitting resolution to be improved simply by increasing the elution temperature.

Definitions

Nucleic acids comprise oligomers or polymers of pentose, connected by phosphoryl groups in phosphodiester linkage between the 5'-OH of one pentose and the 3'-OH of the next pentose, and each pentose carries an aromatic heterocyclic "base" in glycosidic linkage to the 1 carbon. If the pentose is ribose, the nucleic acid is RNA. If the pentose is 2-deoxyribose the nucleic acid is DNA. Each phosphoryl group, except any at the end of a nucleic acid polymer, carries a single negative charge at pH values above about 2 to 3, so that the total negative charge of a nucleic acid is approximately proportional to its length, often expressed in units of nucleotides (nt) or base pairs (bp). Any of a wide variety of bases may be attached to the pentose, but only five predominate in naturally occurring DNA and RNA: adenine ("A"), thymine ("T", only in DNA), uracil ("U", primarily in RNA), guanine ("G"), and cytosine ("C") RNA usually consists of a single ribonucleotide polymer chain. Single stranded DNA is a single, deoxyribonucleotide polymer chain. However, two DNA chains of approximately complementary base sequence can dimerize to form double-stranded DNA. DNA and RNA chains of approximately complementary base sequence can dimerize to form a DNA-RNA hybrid similar in structure to double-stranded DNA.

Often an individual DNA or RNA chain has approximately mutually complementary base sequences in different parts of the polymer chain which permit folding to create locally double-stranded regions. Base complementarily follows simple rules: A can pair with T or U; G can pair with C; the stablest double-stranded structures occur when the two chains have "antiparallel" orientation, such that the 5'-OH end of one chain is base-complementary to the 3'-OH end of the other chain.

An anion-exchange separation is a process wherein fixed positive charges in one phase, usually solid but occasionally liquid, bind negative molecules in a second phase, usually liquid, contacting the first phase. The bound negative molecules can be separated from electrically neutral or positive molecules in the second phase simply by separation of the two phases. They can be separated from one another by contacting the first phase with fresh liquid of different composition from the original second phase such that the new composition weakens the attraction of more weakly bound anions to the first phase more than it does the attraction of more strongly bound anions to the first phase. Strength of anion attraction to the first phase varies directly with total negative charge of the anion. A bound anion is "eluted" when a new liquid succeeds in displacing it from the first phase. If the second phase is repeatedly replaced with liquids which progressively interfere more and more strongly with anion binding to the first phase, the process is called a "gradient elution." If the eluting liquid is changed in composition smoothly over time rather than in successive steps, the gradient elution is "continuous"; otherwise it is "stepwise" elution.

Preferably, the first phase is a solid. This "anion-exchange solid" consists of an electrically neutral "backbone" material which defines its size, shape, porosity, and mechanical properties, and positively charged "functional groups", preferably attached covalently to the backbone. The three most common classes of backbone materials are silica, polysaccharides, and synthetic polyolefins; the two major polyolefin subclasses are polystyrene and the polyacrylics. The latter comprise polymers of various substituted acrylic acid amides ("polyacrylamides") and acrylic acid esters ("polyacrylates"), wherein the acrylic monomer may or may not have alkyl substituents on the 2- or 3-carbon. The two most common positive functional groups are diethyl aminoethyl (DEAE; $[(CH_3CH_2)_2N—CH_2—CH_2—]_n$), attached covalently to the backbone, and polyethylene imine (PEI; $[—CH_2CH_2NH—]_n$), which may be covalently attached or noncovalently adsorbed to the backbone. When a liquid contacting the anion-exchange solid is an aqueous solvent of pH below about 9 to 11, the nitrogen atoms of DEAE and PEI are protonated and therefore positively charged. The lower the pH, the larger the fraction of functional groups that is cationic. The pH region over which most functional groups in a given anion-exchange solid are positively charged depends primarily on the backbone structure and the density of functional groups on the surface of the backbone.

Most commonly in anion-exchange separations, the eluting liquid is an aqueous electrolyte; and gradient elution is accomplished by increasing the concentration of a completely dissociated salt dissolved in the water. Increasing the eluting salt concentration in the anion-exchange solvent weakens the binding of anions, such as nucleic acids, to the anion-exchange solid. For purposes of the present invention, the eluting salt, present in the approximate concentration range of 0.5 to 1.5M, consists of a di-, tri-, or tetra-alkylammonium cation and any of a variety of mono-anions, preferably formate, acetate, chloride, bromide, nitrate, perchlorate, methanesulfonate, dihydrogen phosphate, or ethane sulfonate. Preferably, the alkyl groups on the ammonium cation are methyl or ethyl groups with methyl most preferred. Cations containing both methyl and ethyl groups also are allowed but are harder to prepare than cations containing only one or the other alkyl group. The eluting salt can be prepared as a solid which is dissolved in water to make the eluting solvent, or a solution of eluting salt can be prepared by mixing the acid constituting the protonated monoanion (e.g., formic, acetic, or hydrochloric acid) in equimolar stoichiometry with an aqueous solution of the alkylamine or alkylammonium hydroxide.

The anion-exchange solvents not only contain a dissolved alkylammonium salt but also are buffered at a pH between about 4 and about 9, by adding a weak acid with a pKa (the pH at which half of the acid molecules have lost a proton) between about 3.5 and about 9.5, together with enough base to achieve the desired pH. Preferably, the buffer acid concentration will not exceed about 0.05 M. Also preferably, the buffer acid is itself cationic (i.e., it may be supplied as the salt of the buffer acid cation and the anionic conjugate base of another acid, usually a strong mineral acid), so that its conjugate base is not anionic. An anionic buffer conjugate base might bind to the anion-exchange solid in a way which lowers the pH from the desired value. Particularly preferred buffer acids are provided by the "zwitteronic buffers", originally described by Good et al., 1966, *Biochemistry* 5:467–477, and now commonly available at high purity from biochemical reagent companies.

A preferred anion-exchange separation process is "chromatography", wherein the anion-exchange solid, usually in particulate form, is contacted with continuously flowing anion-exchange solvent, which efficiently carries nucleic acids to the solid for the initial binding reaction and efficiently removes them from the solid as the eluting salt concentration is increased. Particulate anion-exchange solid preferably is packed in a cylindrical column; solvent flows in one end of the column and out the other. An especially preferred mode of liquid chromatography is HPLC, wherein the anion-exchange solid particles are so small (normally 2–10 $\mu$m in diameter) and are packed so tightly that high pressures (hundreds to several thousand pounds per square inch) are needed to force solvent through the column. Such small particles undergo anion-exchange binding and elution reactions very rapidly, permitting separations on the time scale of a few minutes, which still allow the separation from one another of many different nucleic acid species of lengths ranging over one to two orders of magnitude (e.g., 50 to 500 or 5,000 base pairs).

Modes for Carrying out the Invention

Nucleic acids, which may be double-stranded DNA or DNA-RNA hybrids, or single-stranded DNA or RNA, are prepared for anion-exchange chromatography by any of many methods well known to organic chemists, biochemists, and molecular biologists. The DNA or RNA can be synthetic, commonly prepared on solid phases by well known and commercially available procedures. It can be isolated from naturally occurring or artificially grown organisms, living or dead, including organisms or cells obtained in veterinary or human clinical test samples collected for the purpose of disease diagnosis or prognosis, including the monitoring of therapy. Chromatographic analysis of nucleic acids is beneficially simplified if the test sample contains relatively few different and distinct nucleic acid species, so that the elution profile consists of easily resolvable and identifiable peaks standing out above a low background of W absorbance.

A preferred way to provide DNA for chromatographic analysis is the commonly known and practiced polymerase chain reaction (PCR), a method of greatly amplifying the number of molecules of one or a few specific nucleic acid sequences, most commonly in the size range of 50 to 1,000 bp, which is perfectly suited for anion-exchange HPLC separation on the basis of size. The PCR process is described in greater detail in U.S. Pat. Nos. 4,683,195; 4,683,202; 4,800,159; 4,889,818; and 4,965,188, each of which is incorporated herein by reference. Any single PCR tends to generate just one or a few DNA fragments in exactly the concentration range needed for UV absorbance detection of chromatographic peaks, between about $10^{-10}$M and $10^{-7}$M, especially if performed by a Hot Start™ method which uses the wax vapor barrier described in U.S. patent application Ser. No. 481,501, filed Feb. 16, 1990, and incorporated herein by reference. In fact, the present invention, especially in combination with the invention of Ser. No. 481,501, renders anion-exchange HPLC the optimal method for identifying PCR product on the basis of molecular size and for quantitating the yield of PCR product. Another preferred method, used alone or together with PCR, for providing nucleic acid suitable for anion-exchange HPLC analysis is digestion with a restriction endonuclease, a procedure which, for relatively homogeneous DNA, generates a finite and often low number of well defined fragments.

For purposes of the present invention, the test sample nucleic acid applied to the anion-exchange solid does not have to be significantly purified, so long as the test sample does not contain substantial amounts of UV-absorbing substances which bind as tightly as nucleic acids to the anion-exchange solid or which are eluted from the anion-exchange solid in the same salt concentration range effective for eluting the nucleic acids of interest. If such interfering substances are present, they commonly are removed by phenol-chloroform extraction and ethanol precipitation, as described in any commonly available manual of molecular biological techniques. Preferably the sample applied to the anion-exchange solid will have been treated to remove particulate material which might coat or clog the anion-exchange solid. Preferred modes of removing particulates include syringe-driven and centrifuge-driven passage through filters with pore sizes not larger than about 0.45 µm and simple centrifugation for at least 5 minutes of at minimally 10,000 rpm, for example, in a microcentrifuge. Filtration is preferred to centrifugation alone; both processes can be done with any of an abundance of commercially available equipment and disposable devices well known to the chemist, biologist, and molecular biologist. A final detail of test sample preparation is that preferably the nucleic acid should be dissolved in solvent approximating in composition the starting solvent of the gradient elution.

When the chromatographic analyte is double-stranded DNA but the test sample is expected to contain RNA or single-stranded DNA, two preferred modes exist to minimize the potential interference of the latter two types of nucleic acids with the elution profile of the analyte. One mode consists of first treating the test sample with a nuclease specific for RNA (for example, RNase A or RNase T1) or specific for single stranded DNA (for example, nuclease S1 from *Aspergillus oryzae* or mung bean nuclease) under enzyme concentration, temperature, and buffer composition conditions well known in the molecular biological art to protect double-stranded DNA from digestion by the same enzymes.

The other mode consists of first contacting the test sample with a solid material which binds single-stranded DNA under solvent and temperature conditions which strengthen this binding specificity. When the solid material to which the RNA or single stranded DNA has bound is then removed from the remaining liquid test sample (for example, by centrifugation or filtration), the latter is ready for application to the anion-exchange solid. Preferably this contacting is done in a solvent of approximately the same composition as the first solvent used in the chromatographic elution (for example, one containing a dialkylammonium, trialkylammonium, or tetraalkylammonium salt in the approximate concentration range of 0.5–1.0M).

Preferred solids for the specific binding of RNA and single-stranded DNA are nitrocellulose, most commonly available in membrane form, and any of a range of aralkylamines covalently attached to a solid support. Examples of such aralkylamines are phenylethylamine, phenylpropylamine, phenylbutylamine, and naphthyethylenediamine. A particularly convenient solid support is a particulate, epoxide-derivatized, porous or nonporous acrylic matrix, such as HEMA-1000 EH Bio, supplied by Alltech Associates, Inc. The aralkylamine can be reacted with the epoxide-bearing support following instructions supplied by Alltech. A commercially available immobilized aralkylamine is phenylbutylamine Eupergit (Rohm Pharma). However, it has inferior capacity, binding kinetics, and durability as compared to aralkylamine-modified epoxide-bearing HEMA. The amount of solid support used for test sample treatment can be minimized after trial-and-error testing of representative test samples, to simplify the recovery of treated sample from the solid.

One class of test sample wherein the HPLC analyte is double-stranded DNA, wherein interfering RNA or single-stranded DNA is likely to be present, and wherein the treatments just described are likely to be beneficial, is PCR product. If the initial PCR target is contained in genomic DNA, the genomic DNA will be substantially single stranded by the end of PCR thermal cycling. Test samples for PCR amplification often contain RNA as well. PCR product also is accompanied by unreacted primers, which are single-stranded synthetic oligonucleotides.

The anion-exchange solvents of the present invention are made in deionized or glass-distilled water by standard chemical methods. Some eluting salts, such as tetramethylammonium chloride, are commercially available as highly purified solids. However, many must be prepared by mixing equimolar amounts of commercially available bases, such as trimethylamine and tetramethylammonium hydroxide, and acids, such as formic, acetic, nitric, perchloric, methane sulfonic, and ethane sulfonic acids. Component acid and base molarity can be determined in advance by titration to an indicator or potentiometric endpoint with acid or base standardized by the conventional methods of analytical chemistry. Because many of the commercially available alkylammonium salts are hygroscopic and many of the acids and bases are supplied as concentrated aqueous solutions of somewhat variable concentration, precision in solvent preparation is promoted by careful measurement of the conductivity, density, or refractive index of solutions made from carefully titrated components. Then later solutions can be adjusted in concentration to match recorded values of these easily measured physical properties, avoiding the more laborious methods of acid-base titration.

The final concentration of eluting salt in the solvents of the present invention generally will lie between 0.5 and 1.5M. When the eluting salt anion is the conjugate base of a strong acid (for examples, bromide, chloride, nitrate, perchlorate, methanesulfonate, and ethanesulfonate), the eluting salt provides little effective buffer capacity in the 4–9 pH range. Therefore, an additional buffer acid with a pKa within 1 pH unit (preferably within ½ pH unit) of the desired pH is added to the solvent to attain a final concentration, preferably in the range of 0.01 to 0.05M. Particularly preferred buffer acids are the synthetic zwitteronic buffers first described by Good et al, 1966, *Biochemistry* 5:467–477, or cationic acid species (protonated amines) provided as salts of their conjugate bases (amines), such as piperazinium chloride, methyl piperazinium chloride, and ethylene diamine dihydrochloride. Enough additional base must be added to adjust the diluted buffer acid to the desired pH, between 4 and 9. If it is desired to omit all chloride ion from the solvent, equivalent buffering can be obtained by combining the basic amine (e.g., piperazine or ethylene diamine) with enough of the acid used to prepare the eluting salt in order to attain the desired pH value. Lower pH values are likely to denature double-stranded DNA and add positive charges onto A, G, and C bases. Higher pH values tend to reduce the net cationic charge of anion-exchange solids on which the functional group is a primary, secondary, or tertiary amine (for example, diethyaminoethyl groups and polyethylenimine). The pH upper bound of 9 is unnecessary when anion-exchange separation is performed on a matrix carrying quaternary amine functional groups, but pH values above about 10 are unfavorable for double-stranded DNA separations on all anion-exchange solids, because double-stranded DNA tends to be denatured at these high pH values. If the anion-exchange solid has a silica backbone, solvent pH values above about 9 (preferably 7) should be avoided, because they tend to dissolve the backbone.

The anion-exchange solvents of the present invention also may contain additives, such as chelating agents at low concentrations (e.g., EDTA or DTPA in the 0.1–10 mM concentration range) or organic cosolvents such as acetonitrile, formamide and N-methyl pyrrolidone in the 0.1–10% concentration range. The chelator may prevent $Mg^{2+}$, commonly found in nucleic acid preparations and tightly bound to nucleic acid, from interfering with the anion-exchange separation. It may also prevent adventitious iron, a ubiquitous contaminant usually present as a complex ion of the Fe (III) oxidation state, from catalyzing nucleic acid oxidation and cleavage by dissolved $O_2$. An especially preferred chelator for blocking iron-catalyzed oxidation reactions is deferoxamine mesylate, manufactured by Ciba-Geigy and sold by Sigma Chemical Co; an 0.1 mM concentration of this compound is adequately protective. The organic cosolvent may help to block non-ionic interactions between nucleic acid and the anion-exchange solid which interfere with strictly size-dependent separation, more serious with single-stranded DNA and RNA than with double-stranded DNA. The need for such blockage depends on the exact chemistry of the anion-exchange solid backbone. Avoidance of organic cosolvents is preferred, because they commonly are contaminated with oxidatively active iron.

In addition to (a) the presence of an alkylammonium eluting salt in the 0.5 to 1.5M concentration range and (b) buffering in the pH 4–9 range at least equivalent to that provided by 0.01M of a buffer acid with a pKa between 3.5 and 9.5, the anion-exchange solvents of the present invention must meet a third requirement: sufficient UV transparency, especially near 260 nm, to permit spectrophotometric assay of eluted nucleic acid. Absorbances at 260 nm below 0.01 (1 cm path length) relative to distilled water are preferred, absorbances between 0.01 and 0.1 can be tolerated, as long as both buffers in binary gradient elution have approximately the same absorbance. Although there is no strict absorbance cut-off, the degree to which the absorbance exceeds approximately 0.1 increasingly limits the ability to analyze very small amounts of nucleic acid. Therefore, an important part of preparing the anion-exchange solvent is the procurement of UV-transparent components and the storage of components and finished solvents under conditions which disfavor color-forming reactions, principally condensations and oxidations. Preferred conditions are darkness, low temperature, and the use of plastic containers which do not themselves leach UV-absorbing materials (principally antioxidants) into their aqueous contents. Glass containers are acceptable, preferably after soaking in strong mineral acids such as $HNO_3$ to remove absorbed oxidatively active metals such as iron. In the interest of minimizing color formation, it is preferred that the solvents of the present invention contain no organic cosolvents and restrict buffer acid concentration to 0.05M or below, preferably no more than 0.02M. If the solvent pH is between about 7 and about 4 or if a quaternary ammonium functional group is used in the anion-exchange solid, the need for pH buffering in the salt is minimal.

Several treatments of the anion-exchange solvents of the present invention are useful for removing UV-absorbing impurities and for retarding the generation of more such impurities. The UV-absorbing impurities are substantially composed of aromatic organic compounds, which can be removed by contacting the solvents with solids which preferentially adsorb such compounds. Such solids include charcoal, beaded macroreticular polystyrene-divinylbenzene resins like XAD-2, XAD-16, and XAD-4 and acrylic resins like XAD-7 and XAD-8 (Rohm and Haas), and pyrolized beaded macroreticular polystyrene-divinyl benzene resins like Ambersorb® XE-340, XE-347, and XE-348 (Rohm and Haas).

Insofar as solvent coloration (in the UV) results from oxidative side reactions during manufacture and storage, it can be reduced by adsorptive removal of the oxidatively active transition metals, principally Fe, Cr, Co, and Cu, present as impurities and responsible for catalyzing oxidation of solvent components by dissolved oxygen in the solvent. A preferred mode of removing transition-metal contaminants is to contact the solvent or the components from which it is made with a chelating solid. Commercially available chelating solids include Chelex 20 and 100 (BioRad Laboratories), Amberlite® IRC-718 (Rohm and Haas), Chelite® C, N, and P (Serva Biochemicals), Duolite☐ ES 346, ES 466, and ES 467 (Chemical Process Co.), BioRex and Chelex Chelating Membranes (Bio-Rad Laboratories), and Chelating Sepharose Fast Flow (Pharmacia LKB Biotechnology).

Contacting solvents or their components with solids which preferentially bind aromatic compounds can be accomplished by stirring the suspended solid in the solvent or an aqueous concentrate of a component, followed by settling of the solid and decantation or filtration of the supernatant liquid. Alternatively, the solid can be packed in a cylindrical column through which the solvent or a solution of a solvent component is passed at a rate sufficiently low that complete removal of the impurity from the solvent is effected. Some adsorptive solids now are available embedded in porous plastic matrices in filter form, so that effective contacting requires only passage of the anion-exchange solvent through the filter under relatively low applied pressure.

A final useful mode of anion-exchange solvent preparation is microfiltration under vacuum or pressure through a filter of nominal pore size no greater than 0.22 µm, preferably using a sterile filter and receiver. An especially preferred filter material is the 0.02 µm pore size alumina honeycomb membrane made by Anotec Separations Limited and sold by many laboratory reagent and equipment suppliers. Such filtration not only removes particulate materials which might damage chromatographic equipment, but also extends solvent storage lifetime by removing bacteria which might metabolize solvent components.

The anion-exchange solvents and processes of the present invention can be applied to many different anion-exchange solids (membranes, felts, papers, large particles, small particles, porous particles, nonporous particles, spherical particles, irregular particles) in various elution formats (isocratic, step gradient, continuous gradient, salt gradient, pH gradient) commonly known to practitioners of separation art and abundantly supported by the commercial reagent and equipment market. However, analytical HPLC separations on small anion-exchange particles, approximately 2–10 µm in average diameter, most fully benefit from the improvements of the present invention and therefore will be elaborated here.

The most important component of the HPLC equipment is the column and its packing. For analytical separations, column internal diameter will not exceed 10 mm and preferably will not exceed 5 mm; column length will not exceed 50 mm and may be as short as 10 mm. The most preferred packing is a 2.5 µm diameter nonporous organic polymeric (acrylic) material carrying a diethylaminoethyl functional group manufactured by the Tosoh Corporation as "DEAE-NPR", packed in 4.6×35 mm stainless steel columns, and sold by Supelco, the Nest Group, and The Perkin-Elmer Corporation. Less preferred are 8 µm diameter porous (1000 Å or 4000 Å nominal pore size) polystyrene matrices coated with a hydrophilic polymer and carrying a quaternary ammonium group, manufactured by Polymer Laboratories Limited as "PL-SAX", packed in 4.6×50 or 150 mm stainless steel columns, and sold by Polymer Laboratories, The Perkin-Elmer Corporation, and PerSeptive Biosystems. Also less preferred are spherical particles consisting of 10 µm diameter nonporous polystyrene spheres covered with 0.2 µm nonporous polystyrene beads carrying a quaternary ammonium functional group, manufactured and sold by Dionex Corporation as "ProPac PA1" or "NucleoPac PA-100", packed in 4×50 mm plastic columns. Also less preferred are 7 µm diameter porous (4000 Å nominal pore size) silica materials covalently coated either with a diethylaminoethyl-bearing silane or with polyethylenimine, manufactured by Machery-Nagel as "Nucleogen 4000-7" or as "Nucleosil 4000-7", respectively, packed in 4×50 mm stainless steel columns and sold by Rainin. Also less preferred are 2.5 µm diameter nonporous acrylic polymeric beads carrying a diethylaminoethyl functional group, manufactured and sold by the Waters Chromatography Division of Millipore Corporation as "Gen-Pak FAX", packed in 4.6× 100 mm stainless steel columns. Least preferred are 10 µm diameter porous (400–600 Å nominal pore size) acrylic polymeric materials carrying a quaternary amine functional group, manufactured and sold by Pharmacia LKB as "Mono-Q", packed in 5×50 mm glass columns with plastic end-fittings.

In the event that the HPLC analyte is the double-stranded DNA product of the polymerase chain reaction or analytical-scale restriction enzyme digestions, none of the commercially available anion-exchange columns described above is ideally suited to the rapid resolution and identification by size of DNA species. They are all so large that significant peak spreading occurs, especially if the gradient elution is performed on the 2–10 minute time scale. The scale of analytical PCR and restriction digestions is so small that the amount of the resulting DNA injected onto an HPLC column rarely exceeds 1 µg and often approaches 1 ng, far below the capacities of these columns. Furthermore, all of these columns use end-frits which are uniformly porous over the entire column bed cross-section. This design can cause peak spreading because solvent entering the top of the column does not sweep through the entire end-frit at the uniform velocity, instead flowing more rapidly at the center than at the edge. This flow pattern tends to cause analytes which bind to the HPLC adsorbent near the edge of the bed to be eluted more slowly than analytes binding closer to the column axis. The optimal solutions to these column design problems are the following. The chromatographic resins should be packed, by methods well known in the chromatographic art, in cylindrical columns which have diameters between about 2 mm and 6 mm and lengths between about 10 mm and about 30 mm. These columns should have a bottom end frit, the porous part of which completely covers the bed cross-section, and a top end frit, the porous part of which covers only a fraction of the bend cross-section, centered on the column axis. For columns with 4.6 mm internal diameters, a selection of such end frits with restricted-diameter porous plugs is available from Upchurch Scientific.

Given the appropriate anion-exchange column, nucleic acid separations can be run on a wide range of commercially available HPLC equipment with the solvents and processes of the present invention. Preferred for the present invention is a binary gradient solvent delivery system, column thermostating to a precision of at least ±1° C., and UV spectrophotometric detection at 260 nm. However, very fast, efficient resolution of double-stranded DNA in the 50–1,000 bp size range with complete gradient separation in less than 3 minutes can be obtained on the Tosoh DEAE-NPR material if the HPLC equipment meets the following criteria: total volume between solvent mixer and column of less than 100 µL, total flow rate as high as 1.5 mL/min., detector response time below 100 ms, and detector volume below 10 µL. Additionally, it is preferred to reduce the length of tubing between column and detector to less than 2 cm and to thermostat the injector and the tubing which connects the injector to the column.

For most precise use of the anion-exchange solvents of the present invention, a modification of conventional HPLC solvent reservoirs is desirable to minimize evaporation of water and the resulting concentration of eluting salt, which will cause retention times systematically to become shorter as the reservoir is depleted. In this modification, the solvent is enclosed in a collapsible plastic bag within a more rigid reservoir shell, such that there is minimal vapor space over the liquid; the bag is tightly sealed except for the outlet to the HPLC pump. As the reservoir contents are depleted, the bag collapses to maintain minimal solvent contact with air. Preferably, the bag is made of a plastic with minimal permeability to both water and air. Also preferably, the solvent is degassed by methods well known to the chromatographic art before introduction into the bag. Then it should be possible to supply bubble-free solvent to the HPLC pumps without helium sparging, a common practice which increases the opportunity for water evaporation. Commercially available from NOW Technologies (Minneapolis, Minn.) is a 2.5 Liter high-density polyethylene reservoir containing a collapsible Teflon liner, well suited to reducing HPLC solvent evaporation HPLC separation of nucleic acids according to the present invention is effected optimally by (a) equilibrating the column with the starting solvent composition, containing the eluting salt at a concentration between about 0.5 and about 1M, (b) injecting the nucleic acid-containing sample in a volume of about 1 μL to about 100 μL (preferably about 10 μL), (e) initiating a continuous gradient program which increases the eluting salt concentration to a value between about 1M and about 1.5M in an interval between about 2 min. and about 30 min., and (d) recording UV absorbance in the 260 nm region. Optionally, the effluent from the spectrophotometric detector can be collected, in either fractions of equal volume or fractions chosen to contain individual chromatographic peaks. If the elution profile, a graph of absorbance versus time or volume, is recorded digitally, in any of many commercially available microcomputer-based data systems, it can be scaled optimally when the chromatographic run is complete.

The principal matter of judgment in designing an effective HPLC separation, beyond choosing the gradient program, concerns choice of how much nucleic acid to inject. This decision can be optimized by trial and error, especially with short separation times when the test sample is not scarce or expensive. Alternatively, it can be approximated using principles of spectrophotometry and material balance. Modern HPLC spectrophotometric detectors have detection limits below $10^{-4}$ absorbance units (AU) and give strong peaks between $10^{-3}$ and $10^{-2}$ AU in height. Given estimates of (a) the HPLC detector light path, (b) how many distinct peaks a sample is likely to yield, (c) how much mass of nucleic acid a given volume of test sample might contain, and (d) how much volume the peaks are likely to elute in, one can estimate the test sample volume which will give peaks with average absorbances (approximately half of the maximum absorbances) above $10^{-3}$ AU. One μg of double-stranded DNA contains about 0.02 AU mL of 260 nm absorbance. If it is distributed among 10 peaks of approximately 0.1 mL volume, each peak will have an average absorbance of about 0.02 AU with a 10 mm light path or 0.01 AU with a 5 mm light path.

The optimal HPLC gradient elution profile commonly is chosen by trial and error. Once the starting and final concentrations of eluting salt have been found which separate all of the peaks of interest from one another and from the commonly observed "injection spike" of UV-absorbing material which is not retained on the column, the average steepness of the gradient is chosen to effect the separation in the desired interval. The exact shape of the gradient within this interval can be sculpted to enhance resolution of particular peaks or, more often, to create a linear graph of retention time versus the logarithm of DNA fragment size. For anion-exchange separations of double-stranded DNA, the resulting shape will probably be convex-upward.

To facilitate understanding and practice of the invention, a number of illustrative examples are provided below.

EXAMPLE 1

Anion-Exchange HPLC Separation of Double-Stranded DNA with NaCl as Eluting Salt The double-stranded DNA sample was an endonuclease HaeIII digest of the plasmid pBR322 (Boehringer Mannheim), supplied in pH 8.0, 10 mM Tris-Cl, and 1 mM EDTA, diluted ⅕ into 10 mM Tris-Cl, 50 mM KCl, pH 8.3. It includes blunt-ended fragments of the following molecular sizes in base pairs: 51, 57, 64, 80, 89, 104, 123, 124, 184, 192, 213, 234, 267, 434, 458, 504, 540, and 587. The HPLC solvents were the following: Buffer A contained 10 mM cyclohexylaminoethane sulfonic acid (CHES, pKa 9.50 at 25° C.), 500 mM NaCl, pH 8.99; Buffer B contained 10 mM CHES, 700 mM NaCl, pH 8.77. The HPLC equipment consisted of the following: dual Gilson model 302 pumps with 10 WSC heads, a Gilson model 811 dynamic mixer with a 65 μL mixing chamber, a Gilson model 802B manometric module, a Gilson model 231 sample injector with a 50 μL loop, a column heater from Jones Chromatography Ltd., a Perkin-Elmer model LC-95 UV/Visible spectrophotometer detector with an 8 μL (10 mm path) flow cell and a 20 ms response-time setting, a Gilson model 621 data module, controlled and monitored by Gilson model 715 controller software (version 1.0) in a PC-AT clone. Column temperature was measured to ±0.1° C. with a Physitemp model BAT-12 electric thermometer monitoring a teflon-coated 1/20 inch diameter type T thermocouple taped to the column body.

The anion-exchange HPLC column was a Tosoh DEAE-NPR column, 4.6×35 mm, supplied by Supelco or The Perkin-Elmer Corporation. The following solvent gradient program was applied at 1.0 mL/min total flow rate (time from injection, with all gradient segments linear): 8% buffer B (0.516M NaCl) at 0 time; 27% buffer B (0.554M NaCl) at 0.30 min.; 50% buffer B (0.600M NaCl) at 1.30 min.; 50% buffer B at 1.60 min.; 100% buffer B (0.700M NaCl) at 1.70 min.; 100% buffer B at 2.10 min.; 8% buffer B at 2.20 minutes.

FIG. 1 shows a representative elution profile when the column was thermostated at 30.4° C. and 10 μL of the DNA sample (approximately 0.5 μg of DNA) were injected; absorbance was monitored at 260 nm. The dashed line indicates the salt gradient program, left-shifted about 0.3 mL (0.3 minutes) from the elution profile because of the free solvent volume of the mixer, injector, and column. The fragment size identification in bp based on published analyses (Westman et al, 1987, *Anal. Biochem.* 166:158–171, and Kato et al, 1989, *J. Chromatog.* 478:264–268), is given over each peak. It shows abundant evidence of effects of fragment composition on retention time: the 123 bp peak follows the 124 bp peak instead of overlapping it; the 192 bp peak follows the 213 bp peak; the 458 bp peak follows the 504, 540 bp overlapping peaks.

Figure 2:
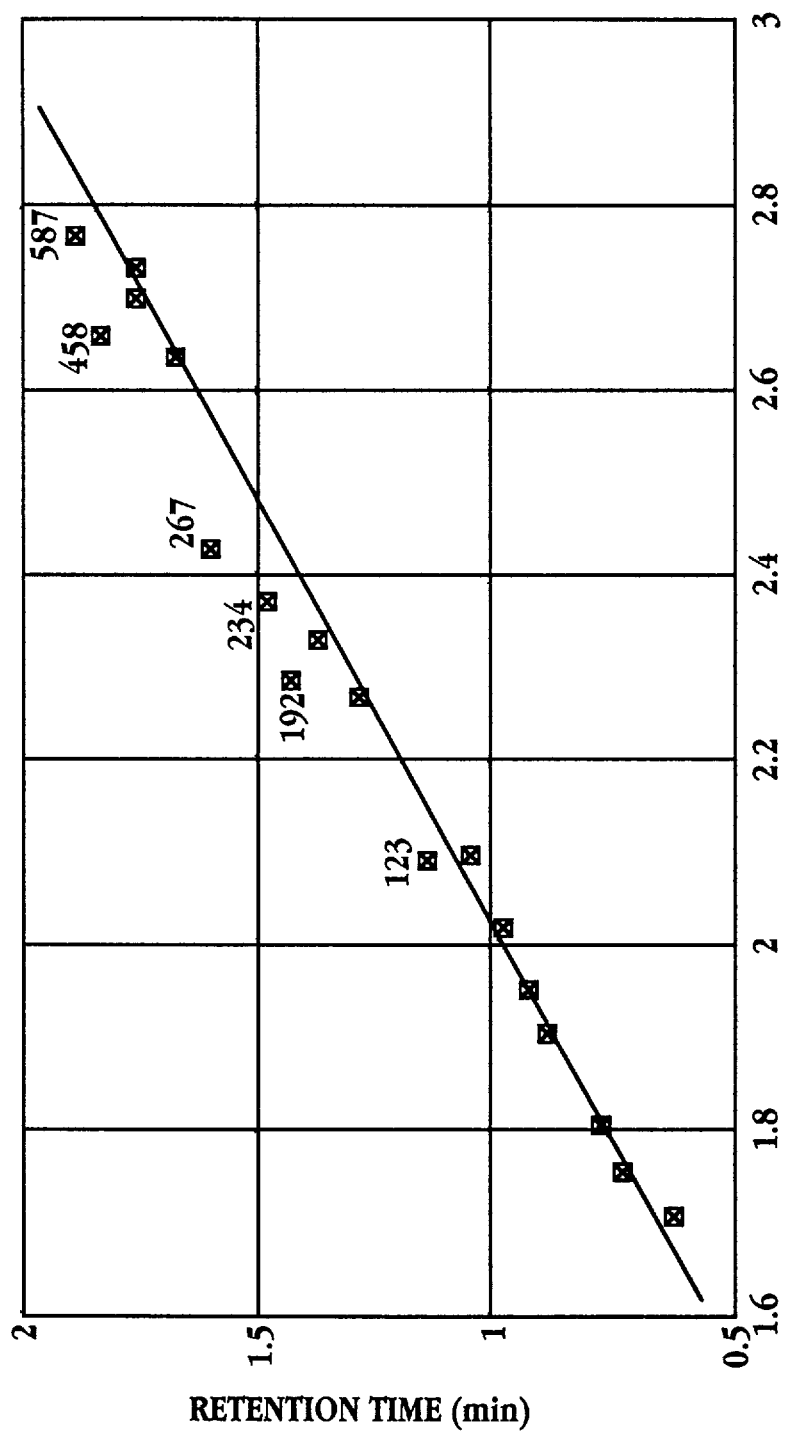
FIG. 2 shows the molecular size calibration curve generated from the elution profile in FIG. 1 when retention time is graphed against the common logarithm of the fragment length (in base pairs), wherein fragment size assignments (indicated over the respective peaks) were made on the basis of agarose gel electrophoresis of the separate collected chromatographic peaks.

FIG. 2 graphs the calibration curve of retention time versus the common logarithm of molecular size in bp. Although most of the peaks lie on an acceptable straight line, six clearly are retained more strongly than would be predicted on the basis of size alone. The 123 bp, 192 bp, and 458 bp peaks are not the only anomalous fragments; the 234 bp, 267 bp, and 587 bp peaks also show signs of non-size dependent additional chemisorption to the chromatographic matrix. Compositional analysis based on the base sequence and restriction map of the pBR322 plasmid shows that the rank order of the anomalous fragments among all of the fragments in this population with respect to A-T content is the following: #1, 458 bp (57.4% A-T); #2, 587 bp (56.7% A-T); #3, 192 bp (52.6% A-T); #4, 267 bp (49.1% A-T); #6, 123 bp (43.9% A-T); #10, 234 bp (41.0% A-T). With the exception of the 234 bp fragment, the anomalously retained fragments tend to be the species with highest A-T content, although none of the fragments possess extremely high A-T content from the perspective of what is available among naturally occurring DNA. Clearly, such a separation cannot be expected to predict accurately the sizes of previously uncharacterized DNA molecules.

Figure 3:
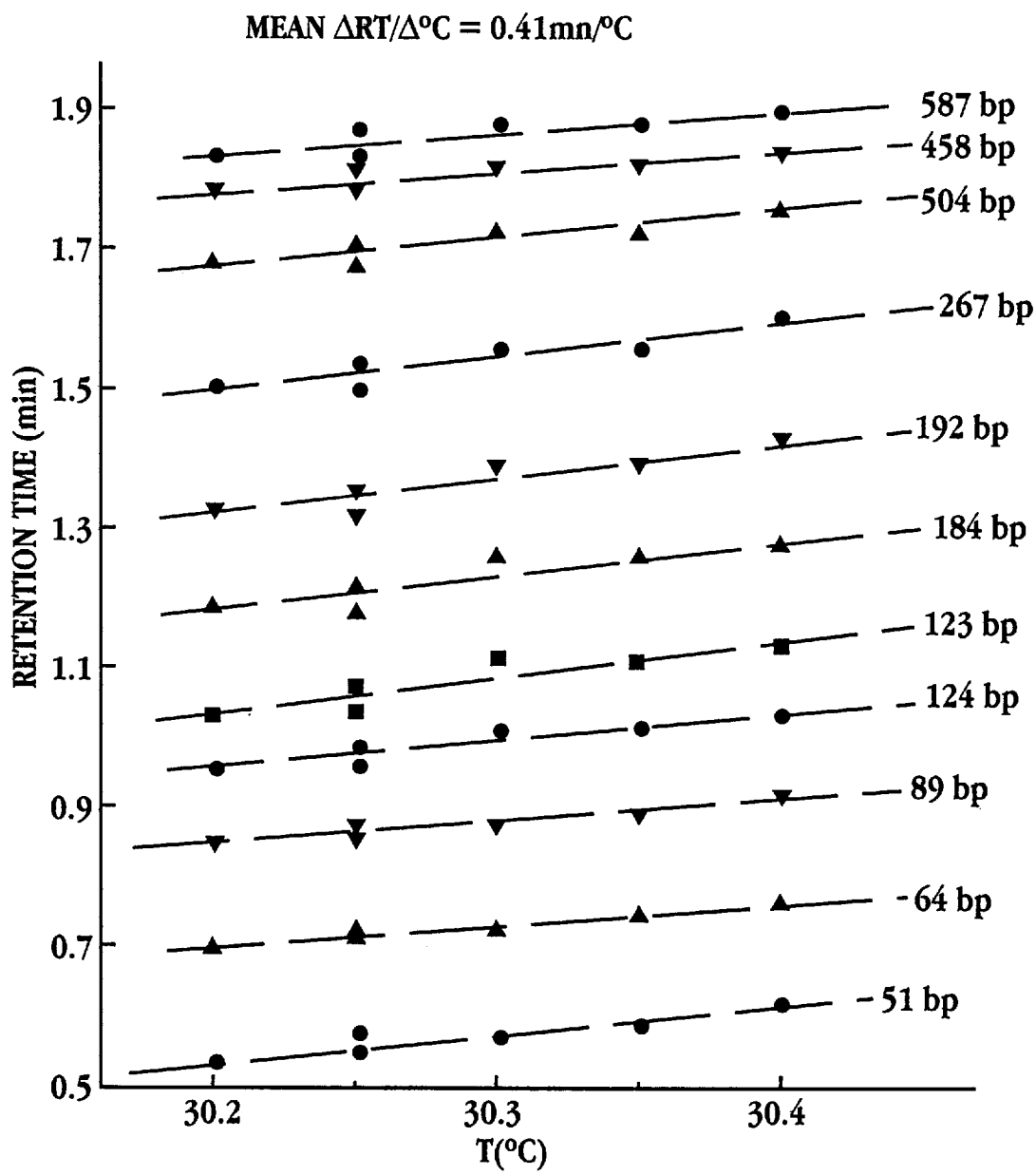
FIG. 3 shows graphs of anion-exchange HPLC retention time against temperature for the restriction fragments of FIGS. 1 and 2, using retention-time data from a series of separations identical to that in FIG. 1 except for the fact that they were thermostated at the different temperatures shown.

FIG. 3 graphs the retention-time temperature dependence of a sampling of the peaks from FIGS. 1 and 2, measured in experiments identical to that just described, except that column temperature was varied over 0.2° C.; the 30.4° C. data points represent averages of six replicate runs. It shows that very small temperature changes can cause quite large retention-time shifts, averaging 0.41 minutes per 1° C. The true significance of this extreme temperature sensitivity can be obtained by dividing the retention-time temperature sensitivity by the slope of FIG. 2 to get the temperature sensitivity of base pair assignment: $\Delta\log bp/\Delta° C.=0.375$. A 0.1° C. temperature uncertainty will generate a 9% uncertainty in fragment size, jeopardizing peak identification and peak matching from run to run.

Other noteworthy features of FIG. 1 are that the salt concentration range over which fragments between 51 and 587 bp (more nearly 51 and 700 bp for peaks without a retention time anomaly) is only 0.08M, and that the slope of the salt gradient approaches zero at the end of the elution. These facts point to the need for extremely precise gradient control from run to run to obtain retention-time and peak-identification precision and to the poor prospect for precisely resolving fragments larger than about 1,000 bp.

These problems—molecular size inaccuracy, molecular size imprecision, and limited molecular size range—illustrate the difficulty of using anion-exchange HPLC to identify double-stranded DNA fragments when conventional HPLC solvents are used. Experiments like those shown here show that lowering the elution pH to 6.0 and varying the column temperature in the 24°–40° C. range do not mitigate the problems shown here, although lowering the pH does remove a different problem. Above pH 9, retention time is very pH-sensitive so that small errors in buffer preparation and the acidification which accompanies $CO_2$ absorption by high-pH buffers can destroy retention-time precision. Between pH 6 and pH 9, retention time is pH-independent, so that pH values below 9 are preferred for greater precision in molecular size assignment.

EXAMPLE 2

Anion-Exchange HPLC Separation of Double-Stranded DNA with Tetramethylammonium Chloride as Eluting Salt The DNA sample, HPLC equipment, HPLC column, HPLC flow rate, spectrophotometer detector settings, and general experimental design were as described in Example 1. The HPLC solvents were the following: Buffer A contained 10 mM 2(N-morpholino) ethane sulfonic acid (MES, pKa=6.15° C. at 20° C.) 800 mM tetramethylammonium chloride (TMAC), pH 6.05; Buffer B contained 10 mM MES, 1500 mM TMAC, pH 6.04. The following gradient program was used, all gradient segments being linear: 12% buffer B (0.884M TMAC) at 0 time; 35% buffer B (1.045M TMAC) at 1.00 min.; 45% buffer B (1.115M TMAC) at 3.00 min.; 100% buffer B at 3.10 min.; 100% buffer B at 3.60 min.; 12% buffer B at 3.70 min.

Figure 4:
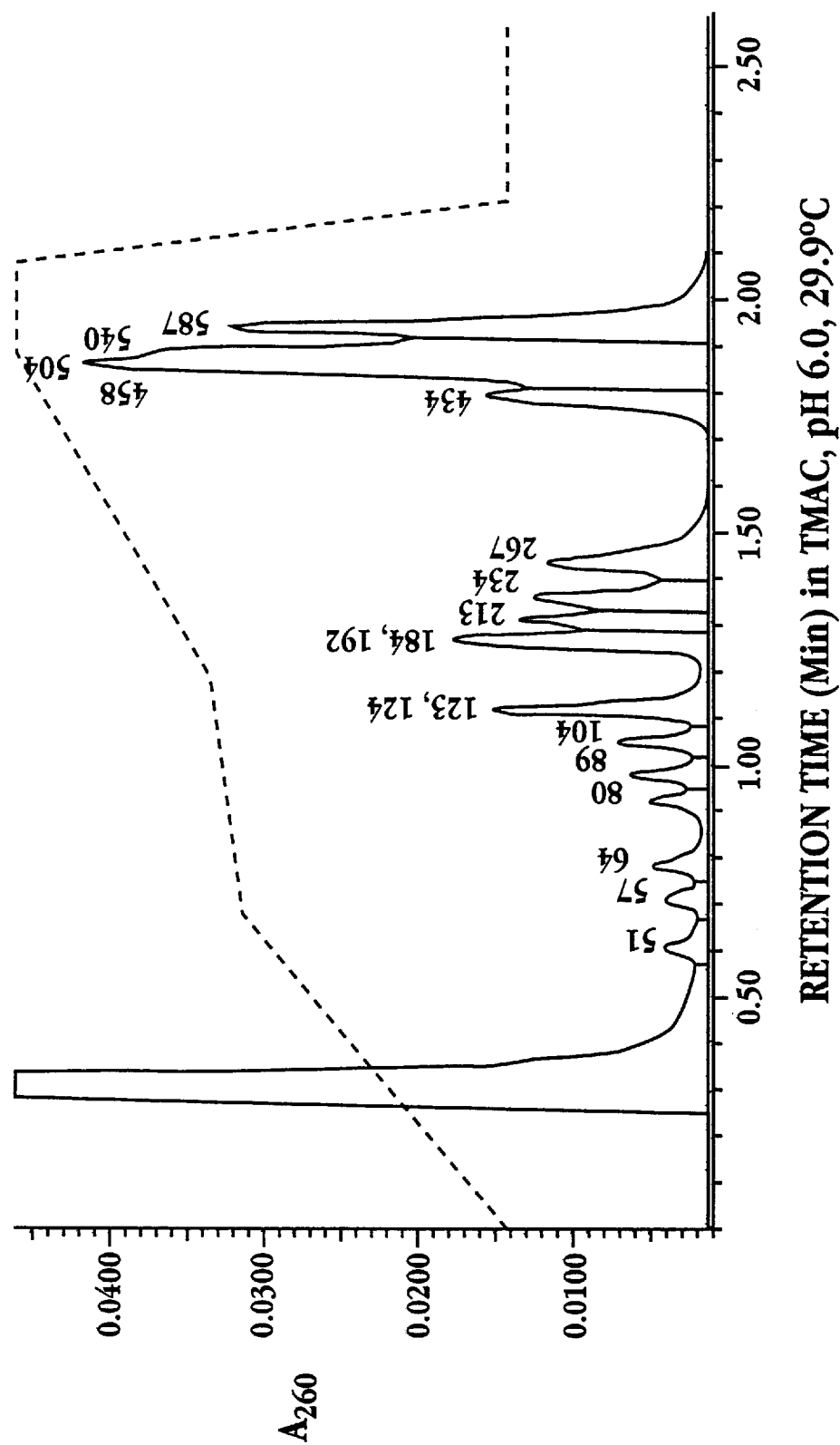
FIG. 4 shows an anion-exchange HPLC elution profile from a separation very similar to that in FIG. 1, wherein tetramethylammonium chloride was used in place of NaCl as the eluting salt.

FIG. 4 shows a representative elution profile when the column was thermostated at 29.7° C. and 10 $\mu$L of the DNA sample were injected. The leading shoulder seen on each peak was a sign of voiding at the top of the column and was eliminated by reversing the column direction or replacing the column; it did not interfere with peak retention-time analysis. This elution profile differs qualitatively from that of FIG. 1. To obtain the fragment size assignments over the peaks in FIG. 4, a salt gradient of similar shape was applied over 9.5 min., a 15-fold larger quantity of the DNA sample was injected, the peaks were collected in separate test tubes, and each collected fraction was electrophoresed in a 4% agarose gel which subsequently was stained with ethidium bromide. The fluorescent band pattern showed clearly that the restriction digest fragments were eluted from the anion-exchange column in strict order of molecular size, justifying the peak assignments in FIG. 4. In fact, the slower, size calibration, chromatographic run gave better peak resolution than seen in FIG. 4, splitting the eighth peak into its 184 and 192 bp components and the thirteenth peak into its 458, 504, 540 bp components, though not to baseline resolution in either case.

Figure 5:
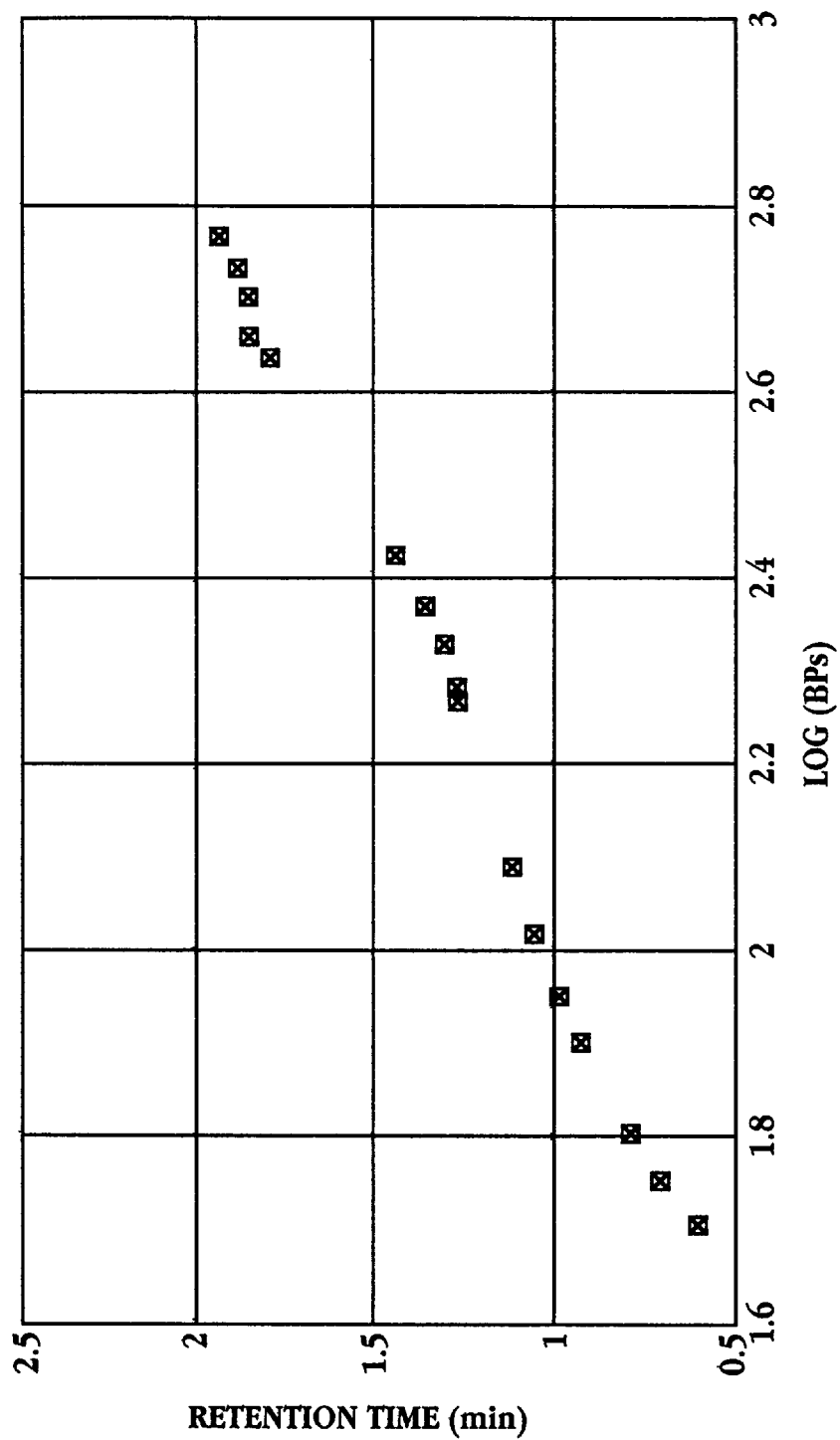
FIG. 5 shows the molecular size calibration curve, like that in FIG. 2, generated from the elution profile in FIG. 4, wherein fragment size assignments (indicated over the respective peaks) were made on the basis of agarose gel electrophoresis of the separate collected chromatographic peaks.

FIG. 5 graphs the calibration curve of retention time versus common logarithm of molecular size in bp for the peaks in FIG. 4. Now the peaks lie on a smooth curve (to the degree permitted by peak resolution). The nonlinearity simply reflects the need to refine the shape of the salt-gradient program; the bilinear gradient between 0 and 3 min. must be replaced by a smoother curve. A linear molecular size calibration curve can be obtained which will accurately predict molecular size without concern about fragment composition.

Figure 6:
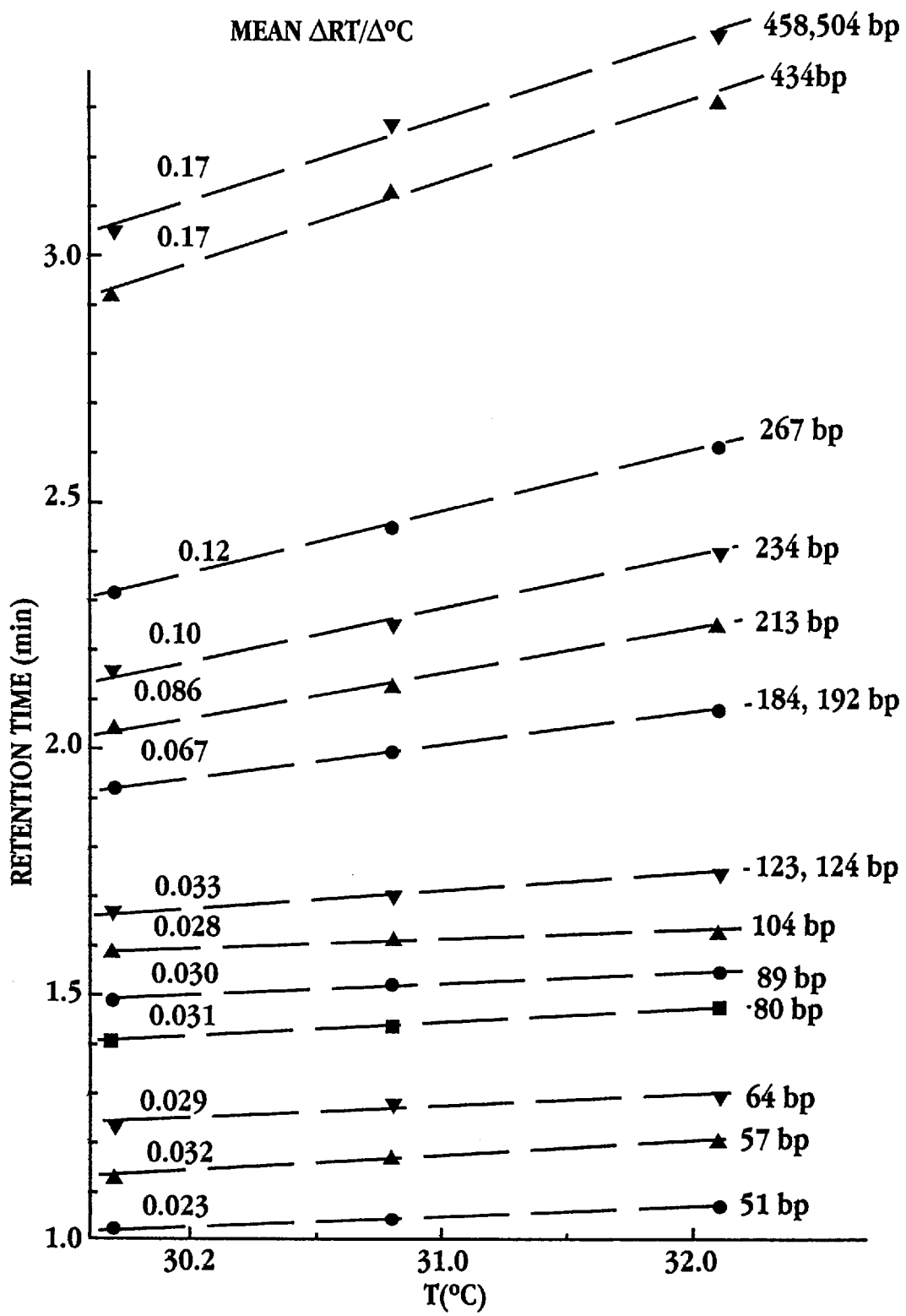
FIG. 6 shows graphs of anion-exchange HPLC retention time against temperature, like those in FIG. 3, using retention-time date from a series of separations like that in FIG. 4 except for the fact that they were thermostated at the different temperatures shown.

FIG. 6 graphs the retention-time temperature dependence of most of the peaks from FIGS. 4 and 5, measured in experiments identical to that of FIGS. 4 and 5 except that the column temperature was varied over 2.4° C. TMAC displays a different retention-time temperature sensitivity than that seen in NaCl in two respects: (a) the slope is greatly decreased from 0.41 min/°C., and (b) the slope now is approximately proportional to fragment size. A logical consequence of the first fact is that TMAC greatly simplifies the thermostating of the HPLC column to obtain acceptable retention time precision. A logical consequence of the second fact is that size resolution is significantly increased as the temperature is raised. In fact, the reduction in retention time temperature sensitivity is greater than inferred from a simple comparison of the graph slopes in FIGS. 3 and 6, because the gradient in the TMAC experiment was 1.9 times longer in duration than that in the NaCl experiment. For a more realistic comparison, the slopes in FIG. 6 should be divided by 1.9.

The effect of the eluting-salt switch on molecular size assignment precision is shown clearly in Table 1 which divides the slopes of FIG. 6 (column 3) by the corresponding slopes of FIG. 5 (column 4) to estimate in column 5 the temperature sensitivity of inferred molecular size; this transformation corrects for the gradient program differences and calibration curve shape differences in the two experiments. The ultimate practical implications are summarized in column 6: in NaCl, the separation must be thermostatted to within 0.01° C. to maintain fragment size precision to within 1% whereas 0.07° C. thermal precision will yield the same size precision or better in TMAC.

TABLE I

Sensitivity of HPLC Molecular Size assignment: NaCl Versus TMAC as Eluting Salt

| Salt | Fragment Size (bp) | $\Delta$R.T./$\Delta$ °C. (min./°C.) | $\Delta$R.T./$\Delta$log bp (min.) | $\Delta$log bp/$\Delta$ °C. (°C. - 1) | $\Delta$ °C. for 1% $\Delta$bp |
|---|---|---|---|---|---|
| NaCl | ALL | 0.41 | 1.09 | 0.38 | 0.011 |
| TMAC | 51–89 | 0.029 | 1.7 | 0.017 | 0.25 |
|  | 104–124 | 0.029 | 1.4 | 0.021 | 0.20 |
|  | 184,192 | 0.067 | 2.8 | 0.024 | 0.18 |
|  | 213 | 0.086 | 2.8 | 0.031 | 0.14 |
|  | 234 | 0.10 | 2.8 | 0.036 | 0.12 |
|  | 267 | 0.12 | 2.8 | 0.043 | 0.10 |
|  | 434–504 | 0.17 | 2.8 | 0.061 | 0.07 |

FIG. 4 reveals other functional benefits of TMAC: the salt concentration sensitivity of retention time is reduced (the eluting salt concentration range is 0.23M instead of 0.08M) and the gradient slope does not approach zero for resolution of the largest fragments. These facts imply that gradient precision will not limit molecular size precision, especially for fragments on the order of 1,000 bp or larger; TMAC should give a larger resolvable molecular size range than NaCl.

The molecular size accuracy benefit of TMAC is preserved when the salt gradient is compressed to give the same total gradient duration as in FIG. 1. Although molecular size resolution appears worse in TMAC than in NaCl (fewer peaks are resolved), the greater resolution in NaCl follows from the composition-dependent retention time anomalies. For reliable and accurate analysis of double- stranded DNA fragments, it is preferable for retention time to be strictly size dependent and for size resolution to be improved by such remedies as (a) increasing HPLC flow rate (e.g., from 1.0 to 1.5 mL/min), (b) minimizing the length and diameter of the tubing which connects the column to the detector, (c) modifying column dimensions to reduce the length/diameter ratio and the total length, and (2) using an column inlet frit with a smaller diameter than the column diameter to minimize dead space at the top of the column.

EXAMPLE 3

Anion-Exchange HPLC Separation of Double-Stranded DNA with Tetramethylammonium Formate (TMAF) as Eluting Salt The DNA sample, HPLC equipment, HPLC column, HPLC flow rate, spectrophotometer detector settings, and general experimental design were as described in Example 1. The HPLC solvents were the following. Buffer A contained 20 mM cyclohexylaminoethane sulfonic acid (CHES) 1.0M TMAF, pH 9.0. Buffer B contained 20 mM CHES 1.5 M TMAF, pH 9.0. The buffers were prepared by adding tetramethylammonium hydroxide to solutions of formic acid plus CHES until pH 9.0 was reached and then adding a small amount of water to reach a final volume containing 20 mM CHES and 1.0 or 1.5M formate. All buffers were vacuum filtered through an Anotec membrane with 0.02 $\mu$m pore size (Whatmen, Inc., Clifton, N.J.). The following gradient program was used, all gradient segments being linear: 6.5% Buffer B at –0.2 min; 6.5% at 0 min; 12.8% at 0.2 min; 18.2% at 0.4 min; 22.8% at 0.6 min; 26.5% at 0.8 min; 29.3% at 1.0 min; 32.0% at 1.2 min; 34.5% at 1.4 min; 37.0% at 1.6 min; 39.4% at 1.8 min; 41.7% Buffer B at 2.0 min; 6.5% at 2.2 min [next injection scheduled at 3.0 min].

Figure 7:
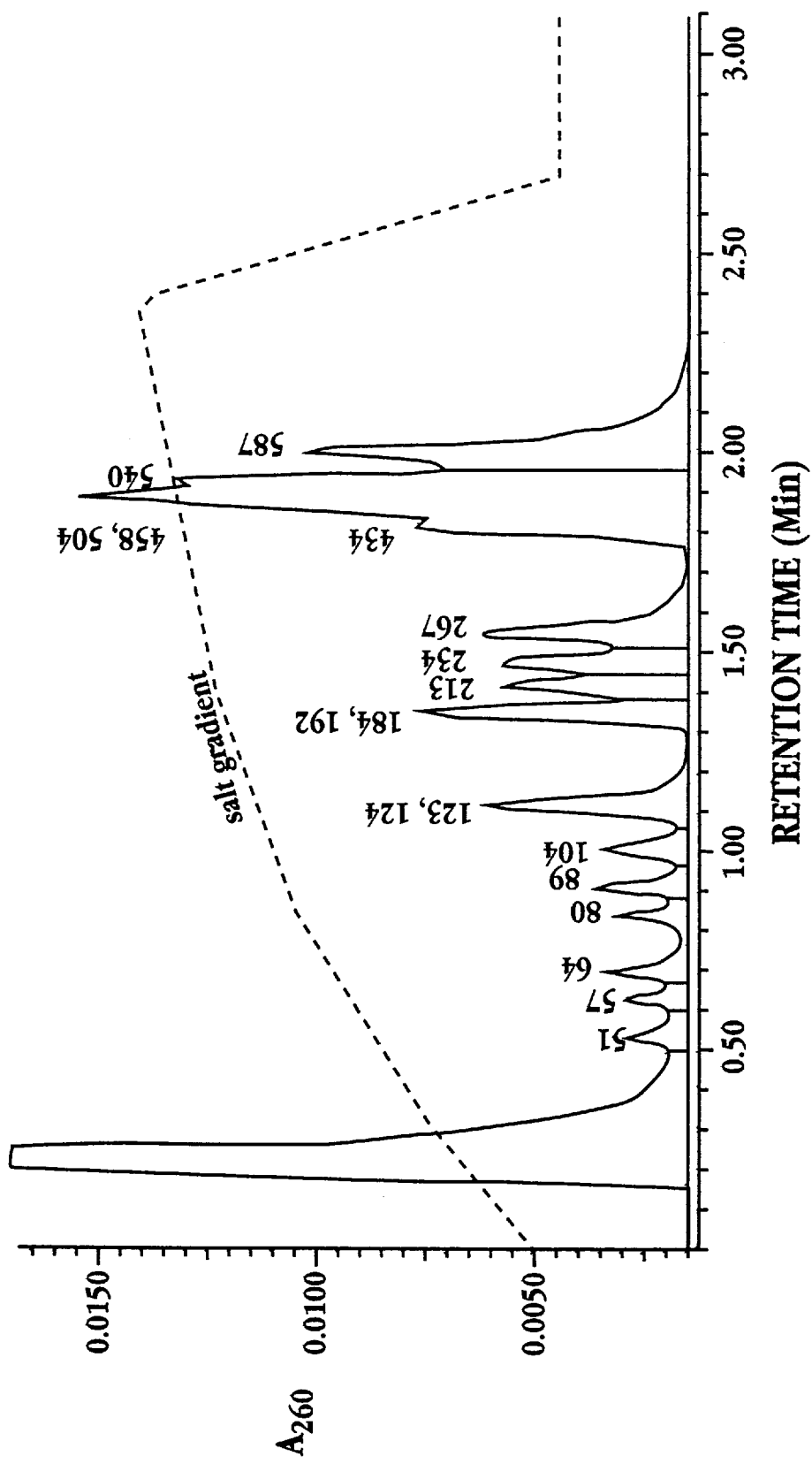
FIG. 7 shows an anion-exchange HPLC elution profile from a separation similar to that in FIG. 1, wherein tetramethylammonium formate was used in place of NaCl as the eluting salt.
Figure 8:
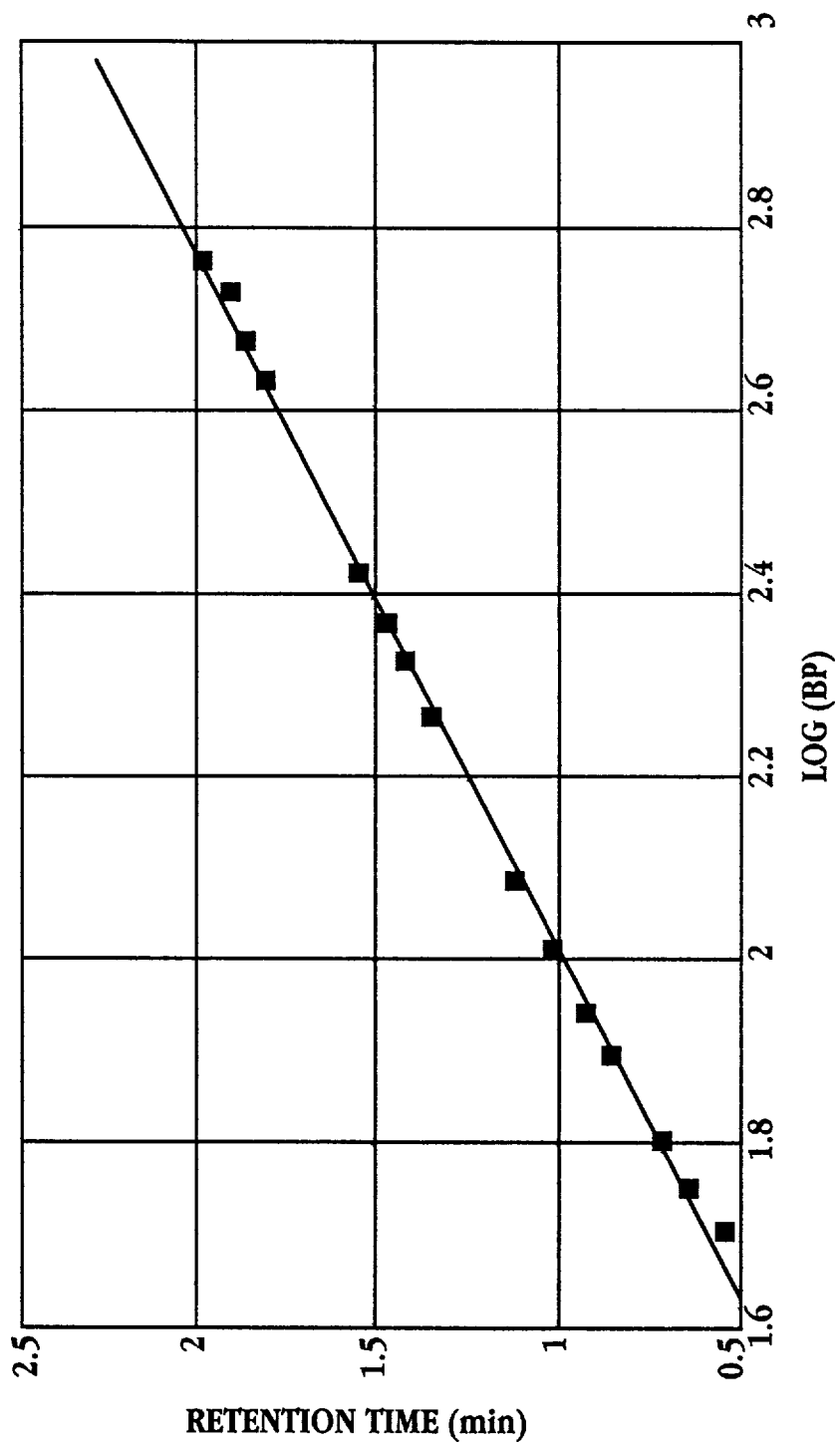
FIG. 8 shows the molecular size calibration curve, like that in FIG. 2, generated from the elution profile in FIG. 7.

FIG. 7 shows a representative elution profile when the column was unthermostatted at approximately 25° C. ambient temperature and 10 $\mu$L of the DNA sample (at 50 $\mu$g/$\mu$L DNA concentration) were injected. FIG. 8 graphs the calibration curve of peak retention time versus common logarithm of molecular size in base pairs for the peaks in FIG. 7. The peaks lie on a straight line which facilitates linear interpolation and extrapolation to evaluate the size of any DNA fragment in the 50–600 bp size range. Changing the eluting salt anion from chloride to formate did not affect the performance improvements caused by replacing sodium with tetramethylammonium as the eluting salt cation. TMAF erases all sequence dependence of the size-ordered elution and reduces the retention-time temperature dependence by almost an order of magnitude (data not shown). Changing the pH from 6.0 (Example 2) to 9.0 effected a significant performance improvement when the chromatographic peak areas were analyzed: increase in recovery of the applied DNA from less than 90% to 99% or greater.

EXAMPLE 4

Extension of DNA Size Resolution to above 20,000 BP

This experiment was designed exactly as in Example 3 except in two regards. The DNA sample contained both a HaeIII digest of pBR322 and a Hind III digest of Lambda, each at 50 $\mu$g/$\mu$L; 10 $\mu$L were injected. The gradient program was identical to that in Example 3 through 1.2 min and continued as follows: 33.0% Buffer B at 1.4 min; 33.7% at 1.6 min; 35.1% at 1.8 min; 37.4% at 2.1 min; 40.5% at 2.3 min; 45.4% at 2.5 min; 51.3% at 2.7 min; 58.2% at 3.0 min; 66.1% at 3.2 min; 75.0% at 3.4 min; 75.0% Buffer B at 4.6 min; 6.5% at 4.8 min.

Figure 9:
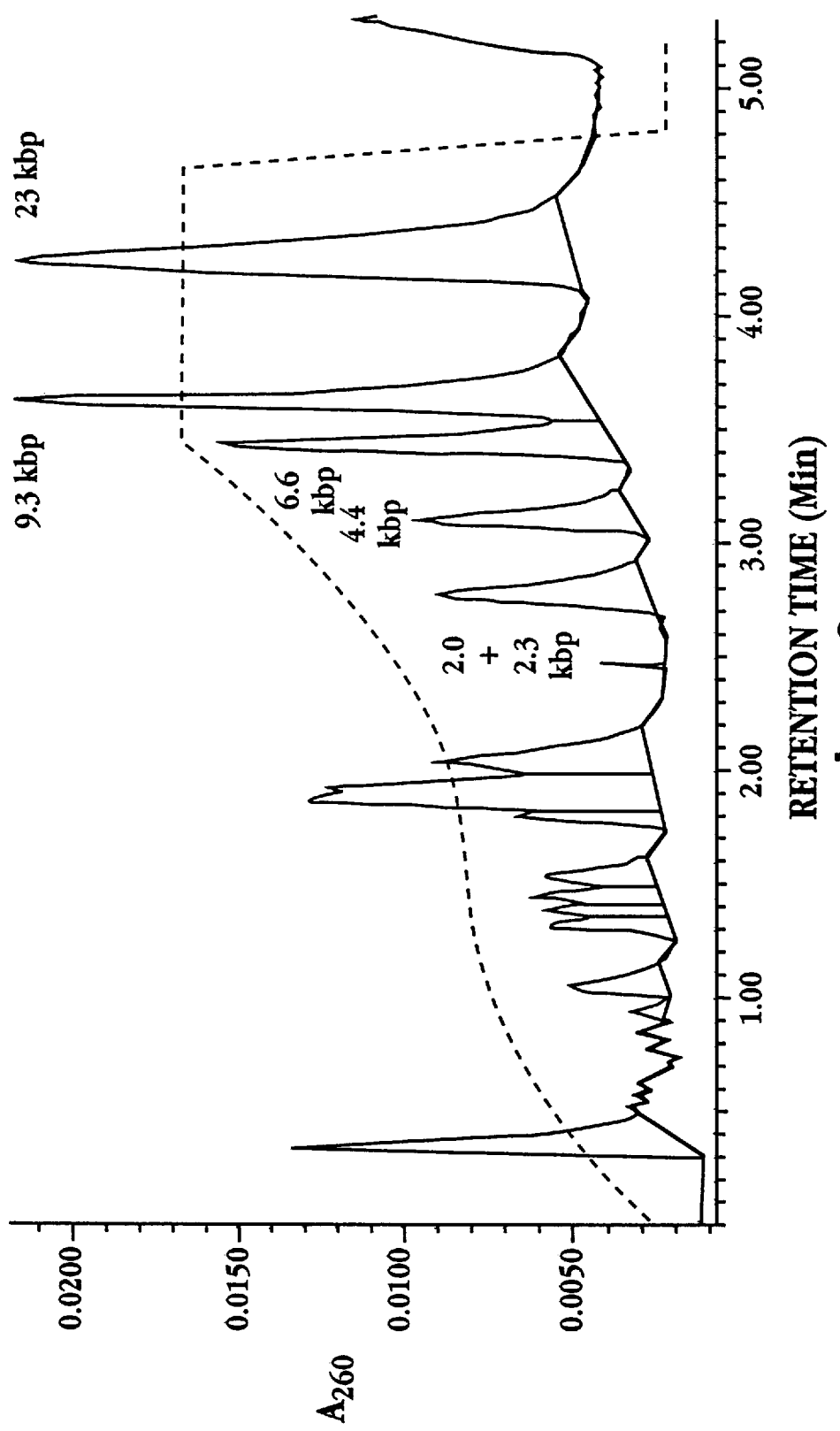
FIG. 9 shows an anion-exchange HPLC elution profile from a separation similar to that in FIG. 7, wherein the DNA sample also contained a similar mass of a Hind III digest of bacteriophage Lambda and the salt gradient was extended to resolve DNA fragments up to about 23,000 bp in size.
Figure 10:
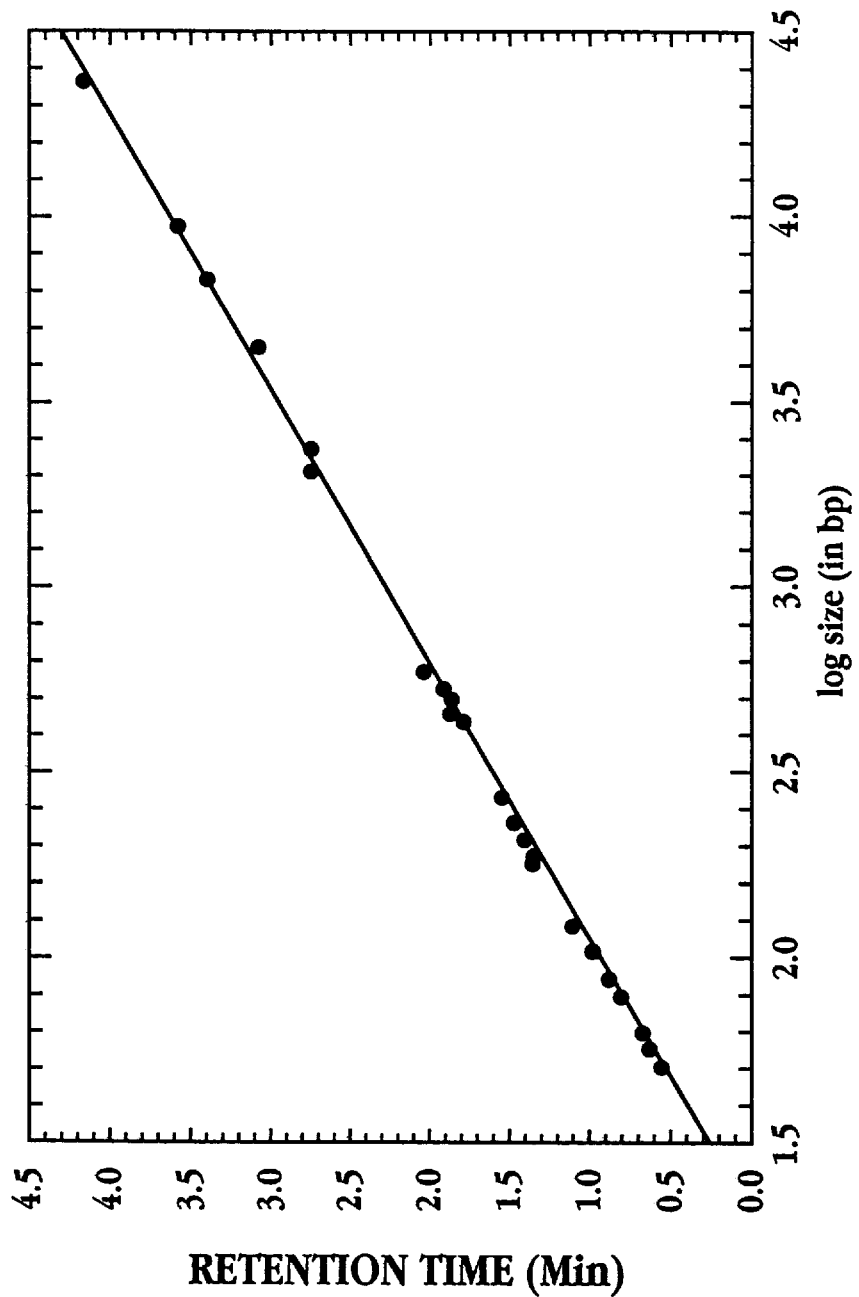
FIG. 10 shows the molecular size calibration curve generated from the elution profile in FIG. 9.

FIG. 9 shows the resulting elution profile, and FIG. 10 graphs the corresponding log size calibration curve. Again, an essentially straight line was obtained for easy size assignment to new fragments in the 50–20,000 bp size range, the practical size range of both PCR products and most restriction fragments. With these results, it is easy to see how the separations of the present invention could be used rapidly to size-characterize and purify practically any PCR product or restriction fragment. A broad-range gradient like that of this Example can be used to find the approximate size range of the fragment, to be followed by a narrow-range gradient (for better size resolution) like that of Example 3, possibly with a gradient program modified for a different narrow size range. Those skilled in the HPLC art could use the gradient information of these examples to design a gradient focusing on any narrower size range.

I claim:

1. An aqueous solvent useful for the anion-exchange chromatography of double-stranded nucleic acids comprising:
   (a) an eluting salt in the approximate concentration range of 0.5 to 1.5M composed of equal concentrations of:
      (1) a tetramethylammonium cation and
      (2) an anion selected form the group consisting of formate and nitrate, and
   (b) a buffer acid with a pKa in the approximate range of 3.5. to 9.5, which acid has a concentration not exceeding approximately 0.05M;
   wherein the eluting salt and the buffer are components of an aqueous solution.

2. The composition of claim 1 wherein said anion is formate.

3. The solvent of claim 1, wherein the buffer acid is cationic and has a conjugate base that is cationic or neutral in charge.

4. A composition comprising the combination of the solvent of claim 1 with an anion-exchange solid.

5. The composition of claim 4, wherein said solid comprises a polyacrylic backbone.

6. The composition of claim 4, wherein said solid comprises diethylaminoethyl functional groups.

7. The composition of claim 4, wherein said solid comprises polyethyleneimine functional groups.

8. The composition of claim 4, wherein said solid comprises particles with an average diameter between approximately 10 $\mu$m and 2 $\mu$m.

9. The composition of claim 4, wherein said solid is substantially nonporous.

10. The composition of claim 4, wherein said solid comprises a polystyrene backbone.

* * * * *